United States Patent
Tremblay et al.

(10) Patent No.: US 10,005,804 B2
(45) Date of Patent: *Jun. 26, 2018

(54) TC-PTP INHIBITORS AS APC ACTIVATORS FOR IMMUNOTHERAPY

(71) Applicant: THE ROYAL INSTITUTION FOR THE ADVANCEMENT OF LEARNING / MCGILL UNIVERSITY, Montreal (CA)

(72) Inventors: Michel L. Tremblay, Montreal (CA); Claudia Penafuerte, Montreal (CA); Matthew Feldhammer, Montreal (CA); George Zogopoulos, Montreal (CA); Cameron Black, Baie d'Urfe (CA); Brian Kennedy, Kirkland (CA)

(*) Notice: Subject to any disclaimer, the term of this patent is extended or adjusted under 35 U.S.C. 154(b) by 0 days. days.

This patent is subject to a terminal disclaimer.

(21) Appl. No.: 15/709,688

(22) Filed: Sep. 20, 2017

(65) Prior Publication Data
US 2018/0072763 A1    Mar. 15, 2018

Related U.S. Application Data

(63) Continuation of application No. 15/122,031, filed as application No. PCT/CA2015/000131 on Feb. 27, 2015, now Pat. No. 9,828,399.

(60) Provisional application No. 61/945,922, filed on Feb. 28, 2014.

(51) Int. Cl.
| | |
|---|---|
| C07F 9/6553 | (2006.01) |
| A61K 31/67 | (2006.01) |
| A61K 35/15 | (2015.01) |
| A61K 31/662 | (2006.01) |
| A61K 39/39 | (2006.01) |
| A61K 45/06 | (2006.01) |
| A61K 39/00 | (2006.01) |
| C12N 9/16 | (2006.01) |

(52) U.S. Cl.
CPC ...... *C07F 9/655354* (2013.01); *A61K 31/662* (2013.01); *A61K 31/67* (2013.01); *A61K 35/15* (2013.01); *A61K 39/0011* (2013.01); *A61K 39/39* (2013.01); *A61K 45/06* (2013.01); *C12N 9/16* (2013.01); *A61K 2039/5154* (2013.01)

(58) Field of Classification Search
None
See application file for complete search history.

(56) References Cited

U.S. PATENT DOCUMENTS

2006/0247210 A1    11/2006    Zhang et al.

FOREIGN PATENT DOCUMENTS

| | | |
|---|---|---|
| CA | 2492964 | 3/2001 |
| CA | 2382406 | 2/2004 |
| WO | 2006055525 | 5/2006 |
| WO | 2008089581 | 7/2008 |
| WO | 2012149413 A1 | 11/2012 |

OTHER PUBLICATIONS

Hemal A. Bhuva et al.; "Synthesis and cytotoxic activity of some novel substituted 2-phenyl-1, 3-benzothiazoles", Journal of Pharmacy Research 2010, 3(5), 980-983.
ISR from the corresponding International Patent Application PCT/CA2015/000131 dated Jun. 3, 2015.
Dewang et al.; "Protein Phosphatases and their Inhibitors", Current Medicinal Chemistry, vol. 12, No. 1, Jan. 1, 2005, pp. 1-22, Abstract only.
Heneberg, P.; "Use of Protein Tyrosine Phosphatase Inhibitors as Promising Targeted Therapeutic Drugs", Current Medicinal Chemistry, vol. 16, No. 6, Feb. 2009, pp. 705-733.
Masahiko et al.; "Market Suppression of T Cells by a Benzothiophene Derivative in Patients with Human to T-Lymphotropic Virus Type I-Associated Myelopathy/Tropical Spactic Paraparesis", Chinical and Diagnostic Laboratory Immunology, May 1999, pp. 316-322.
Supplementary Partial European Search Report issued from the corresponding European Patent Application No. 15755646.5 dated Jul. 5, 2017.
Gagoś: "Molecular organization of 2-(2,4-dihydroxylphenyl)-5,6-dichlor 1,3-benzothiazole in monomolecular layers formed with diphytanoylphosphatidylcholine: A linear dichroism—FTIR study", Biochimica et Biophysica Acta, vol. 1778, Aug. 2008, pp. 2520-2525.
Bhuva et al.: "Synthesis, anticancer activity and docking of some substituted benzothiazoles as tyrosine kinase inhibitors", Journal of Molecular Graphics and Modelling, vol. 29, Apr. 2010, pp. 32-37.
Office Action of corresponding Chinese Application No. 201580023358.9, dated Dec. 5, 2017.

*Primary Examiner* — Bong-Sook Baek
(74) *Attorney, Agent, or Firm* — Benoit & Cote Inc.; Mathieu Miron

(57) ABSTRACT

The invention encompasses the novel class of compounds represented by the Formula (I) below, which are inhibitors of the TC-PTP enzyme. The invention also encompasses pharmaceutical compositions which include the compounds shown above and methods of treating or preventing TC-PTP mediated diseases, including cancer, via their use in the activation of antigen-presenting cells, like dendritic cells, for applications in the immunotherapeutic treatment of diseases.

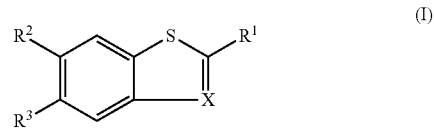

9 Claims, 1 Drawing Sheet

TC-PTP INHIBITORS AS APC ACTIVATORS FOR IMMUNOTHERAPY

CROSS-REFERENCE TO RELATED APPLICATIONS

This application is a Continuation application of U.S. patent application Ser. No. 15/122,031, which is a US National Phase application under 35 USC § 371 of PCT/CA2015/000131, filed Feb. 27, 2015, which claims priority from and the benefit of U.S. Provisional Application No. 61/945,922, filed on Feb. 28, 2014, the specifications of which are hereby incorporated by reference in their entireties.

FIELD OF THE INVENTION

This invention relates to novel inhibitors of TC-PTP and their use in activating antigen-presenting cells, like dendritic cells for application immunotherapy treatment of disease.

BACKGROUND

An important aspect of immunotherapy or cell therapy utilizes modified antigen-presenting cells (APC) to elicit an immune response in patients. Dendritic cells (DC), the most potent APCs, are essential for the induction and maintenance of this response and are central to the development of effective immunotherapies towards treating animal and human infectious diseases as well as different human cancers. For example, tumor tissues, DCs can engulf apoptotic or necrotic tumor cells, process and present tumor antigens to induce tumor specific T cell responses and immunity. However, despite this potent defensive barrier, tumors progress, metastasize, and eventually can kill the host. Immunosuppressive factors secreted in the tumor microenvironment contribute to the evasion of immune surveillance. Such factors can profoundly affect DC function. Strong evidence indicates that DC defects in cancer are due to abnormal differentiation and maturation of myeloid cells, which has deleterious effects on T cell activation and antitumor response. Therefore, the efficacy of DC-based immunotherapies is compromised by immunosuppressive tumor microenvironment. Cancer patients display a significant reduction of mature and functional DCs, as well as accumulation of immature DCs (iDCs) or immature myeloid cells (iMCs, DC progenitors from the bone marrow), which has been associated with increased plasma levels of suppressive tumor-derived factors. DCs derived from cancer patients express no or low levels of costimulatory molecules CD80 and CD86. Consequently, the major hurdle in DC immunotherapy is that iDCs or iMCs induce T cell tolerance or anergy, which consistently affects the development of an effective antitumor response while favouring tumor growth and metastasis.

Dysregulation of one of the critical pathways essential for the activation of the immune response, the cytokine-activated janus kinase-signal transducer and activator of transcription (JAK-STAT) pathway has been identified as one of the key factors responsible for the abnormal DC differentiation and function in cancer. This pathway, controls DC differentiation, maturation, activation and DC-dependent induction of $T_H1$-cell differentiation. There are four members in the Jak family of tyrosine kinases: Jak1, Jak2, Jak3, and Tyk2 [1,2]. Jak kinases are constitutively associated with cytokine receptors and are activated by the binding of a cytokine to its cell-surface receptor. Once activated the Jak kinase phosphorylates specific tyrosine residues on the receptor providing binding sites for STATs. STATs, consisting of 7 members: Stat1, Stat2, Stat3, Stat4, Stat5a, Stat5b, and Stat6, are a group of latent cytoplasmic transcription factors, which reside in an inactive form in the cytoplasm. They are activated by binding to the phosphorylation sites on cytokine receptors and are subsequently phosphorylated on a specific tyrosine residue by Jak. When phosphorylated they disassociate from the receptor, dimerize and enter the nucleus to induce expression of target genes. In addition to cytokine and chemokine receptors, JAK-STAT signaling can also be initiated directly by receptor tyrosine kinases such as Epidermal growth factor receptor, platelet derived growth factor receptor and others. It is the combination of these different stimuli, positive and negative; as well as the recognition of immunogens that lead to optimal potentiation of DCs and the downstream activation of Th-1 cell differentiation.

Currently, the generation of DCs for immunotherapy treatment by in vitro differentiation of monocytes from peripheral blood and their subsequent maturation and activation, is through the use of various cytokine cocktails. The synergistic interaction between GM-CSF and IL-4 induces JAK-STAT pathway activation during DC differentiation, IL-4 mediates its effects primarily through STAT6 activation and GM-CSF activates STAT1 and STAT5. STAT6 is constitutively activated in immature DCs and declines as the cell differentiates into a functionally mature DC, whereas STAT1 signaling is more robust in mature DCs, correlating with upregulation of costimulatory molecules expression and IL-12 production. STAT5 is required for differentiation of DCs during maturation. One additional STAT required for the early phases of DC differentiation, as well as commitment of common lymphoid progenitors (CLP) and common myeloid progenitors (CMP) to the DC lineage is STAT3. DC differentiation inversely correlates with STAT3 activation hence mature DCs show low levels of STAT3 activation STAT3 hyperactivation however results in inhibition of DC maturation/activation in response to diverse stimuli. Most of the tumor-derived factors take advantage of this pathway to promote abnormal DC differentiation by inducing STAT3 hyperactivation. Activated STAT3 decreases intracellular major histocompatibility complex II (MHCII) alpha/beta dimers, and H2-DM levels in DCs by increasing cathepsin S activity. In addition, STAT3 hyperactivation also inhibits LPS-induced interleukin (IL)-12p40 gene expression and affects NF-kB recruitment to the IL-12p40 promoter leading to a build-up of functionally impaired and immature myeloid cells with a high immunosuppressive potential. These reports indicate that STAT 3 activation must be tightly controlled in order to maintain the balance between inhibitory and activating signals.

PTPs are a family of transmembrane or intracellular enzymes that control multiple cellular regulatory processes by dephosphorylating phospho-tyrosine substrates. There are 107 PTPs in the human genome and several reviews have described in detail the members of this gene family. TC-PTP (PTPN2) is found principally as a ~45 kD intracellular protein that localizes primarily to the nucleus and belongs to the class I subfamily of phospho-tyrosine specific PTPs. Although TC-PTP is ubiquitously expressed, highest expression is observed in all hematopoietic cells [1, 3, 4]. In vitro analysis indicates that TC-PTP negatively regulates cytokine signaling by inhibiting JAK-STAT pathways. Currently, JAK1, JAK3, STAT1, STAT3, and STAT5a/b have been identified as putative TC-PTP targets downstream of cytokines such as IL-2, IL-6, IL-4, and IFN-γ [1, 2, 5]. Consequently, TC-PTP has been identified as a critical negative regulator of DC activation, suggesting that inhibitors of this enzyme may be beneficial in the activation of these cells for immunotherapy treatment of disease.

SUMMARY

According to an embodiment, there is provided a compound of structural Formula I, or a pharmaceutically acceptable salts thereof, and stereoisomers thereof:

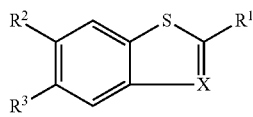

I wherein:
X is selected from CH and N;
$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (b) —(C=O)$R^4$; (c) —CN; (d) —(C=O)$OR^4$; (e) —(C=O)$NHR^4$; (f) —(C=O)$NR^5R^6$; and (g) aryl or heteroaryl wherein the aryl and heteroaryl group itself may be optionally substituted with 1-3 substituents independently selected from (i) halogen, (ii) —(C=O)$OC_{1-3}$ alkyl optionally substituted with 1-3 halogens, (iii) —COOH (iv) $C_{1-3}$ alkyl optionally substituted with 1-3 halogens, (v) —$OC_{1-3}$ alkyl optionally substituted with 1-3 halogens, (vi) —$SO_x$Me, (vii) —CN, and (viii) —$SO_2NH_2$;
$R^2$ and $R^3$ are independently selected from the group consisting of (a) halogen; (b) difluoromethylphosphonic acid;
$R^4$ is selected from the group consisting of (a) H; (b) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (d) aryl or heteroaryl wherein the aryl or heteroaryl group itself may be optional substituted by 1-3 halogens, $C_{1-3}$ alkyl or $C_{1-3}$ haloalkyl;
$R^5$ and $R^6$ are independently selected from the group consisting of (a) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (b) aryl or heteroaryl wherein the aryl or heteroaryl group itself may be optionally substituted by 1-3 halogens, $C_{1-3}$ alkyl or $C_{1-3}$ haloalkyl:
$R^5$ and $R^6$, together with the nitrogen atom to which they are attached may be joined to form a 5- to 7-membered ring, which may be substituted with 1-3 groups independently selected from (i) halogen, (ii) —(C=O)$OC_{1-3}$ alkyl, (iii) —(C=O)OH (iv) $C_{1-3}$ alkyl optionally substituted with 1-3 halogens, (v) —$OC_{1-3}$ alkyl optionally substituted with 1-3 halogens, (vi) —OH, (vii) $C_{1-3}$ hydroxyalkyl, (viii) aryl or heteroaryl wherein the aryl or heteroaryl group itself may be optionally substituted by 1-3 halogens, $C_{1-3}$ alkyl or $C_{1-3}$ haloalkyl; and
x is an integer from 0 to 2.
The compound may be a compound of structural Formula Ia, or a pharmaceutically acceptable salts thereof, and stereoisomers thereof,

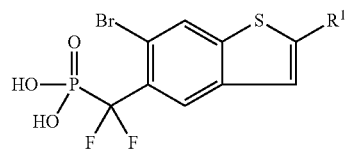

Ia wherein;
$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, and —CN; (b) —(C=O)$R^4$; (c) —CN; (d) —(C=O)$OR^4$; (e) —(C=O)$NHR^4$; and (f) —(C=O)$NR^5R^6$;
$R^4$ selected from the group consisting of (a) H; and (b) $C_{1-3}$ alkyl optionally substituted with 1-5 halogens;
$R^5$ and $R^6$ are it selected from the group consisting of $C_{1-3}$ alkyl optionally substituted with 1-5 halogens and optionally with one group selected from —OH, and —$OC_{1-3}$ alkyl optionally substituted with 1-3 halogens; and
$R^5$ and $R^6$, together with the nitrogen atom to which they are attached may be joined to form a 5- to 7-membered ring, which may be substituted with a 1-3 groups independently selected from (i) halogen, (ii) $C_{1-3}$ alkyl optionally substituted with 1-3 halogens, (iii) —$OC_{1-3}$ alkyl optionally substituted with 1-3 halogens, (iv) —OH, and (vii) $C_{1-3}$ hydroxyalkyl.
The compound may be a compound of structural Formula Ib, or a pharmaceutically acceptable salts thereof, and stereoisomers thereof;

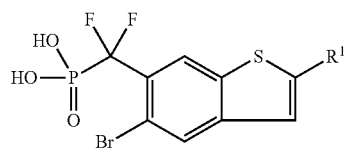

Ib wherein:
$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, and —CN; (b) —(C=O)$R^4$; (c) —CN; (d) —(C=O)$OR^4$; (e) —(C=O)$NHR^4$; and (f) —(C=O)$NR^5R^6$;
$R^4$ is selected from the group consisting of (a) H; and (b) $C_{1-3}$ alkyl optionally substituted with 1-5 halogens;
$R^5$ and $R^6$ are independently selected from the group consisting of $C_{1-3}$ alkyl optionally substituted with 1-5 halogens and optionally with one group selected from —OH, and —$OC_{1-3}$ alkyl optionally substituted with 1-3 halogens; and
$R^5$ and $R^6$, together with the nitrogen atom to which they are t attached may be joined to form a 5 to 7-membered ring, which may be substituted with a 1-3 groups independently selected from (i) halogen, (ii) $C_{1-3}$ alkyl optionally substituted with 1-3 halogens, (iii) —$OC_{1-3}$ alkyl optionally substituted with 1-3 halogens, (iv) —OH, and (vii) $C_{1-3}$ hydroxyalkyl.
The compound may be a compound of Formula I, or a pharmaceutically acceptable salt thereof, selected from the following compounds:

The compound may be a compound of Formula Ia, or a pharmaceutically acceptable salt thereof, selected from the following compounds:

The compound may be a compound of Formula, or a pharmaceutically acceptable salt thereof, selected from the following compounds:

The compound may be a compound of Formula Ib, or a pharmaceutically acceptable salt thereof, wherein the compound is

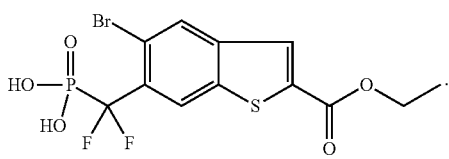 [SMILES: CCOC(=O)c1cc2cc(Br)c(C(F)(F)P(=O)(O)O)cc2s1]

According to another embodiment, there is provided a pharmaceutical composition comprising a compound of the present invention, or a pharmaceutically acceptable salt thereof, and a pharmaceutically acceptable carrier.

According to an the embodiment, there is provided a use of a compound the present invention or a pharmaceutically acceptable salt thereof for the manufacture of a medicament for inhibiting TC-PTP and activating antigen presenting cells for treatment of a disease or condition in a patient.

According to another embodiment, there is provided a use of therapeutically effective amount of a compound of the present invention, or a pharmaceutically acceptable salt thereof, for preventing or treating a TC-PTP mediated disease or condition in a patient in need of treatment.

The TC-PTP-mediated disease or condition may be an immunosuppressive disease, and the immunosuppressive disease may be AIDS, TC-PTP-mediated disease or condition may be a cancer, and the cancer may be prostate cancer, breast cancer, ovarian cancer, multiple myeloma, brain cancer, glioma, lung cancer, salivary cancer, stomach cancer, thymic epitherlial cancer, thyroid cancer, leukemia, melanoma, lymphoma, gastric cancer, pancreatic cancer, kidney cancer, bladder cancer, colon cancer and liver cancer. The TC-PTP-mediated disease or condition may be an infectious disease, and the infectious disease may be a viral infection, a bacterial infection, a fungal infection, a parasitic infection, or a combination thereof. The viral infection may be a cytomegalovirus infection, an Epstein-Barr virus infection, a hepatitis B infection, a hepatitis C virus infection, a herpes virus infection, a human immunodeficiency virus infection, a human T lymphotropic virus infection, a lymphocytic choriomeningitis virus infection, a respiratory syncytial virus infection, rhinovirus infection, or a combination thereof. The bacterial infection may be a *Corynebacterium* infection, an *Enterococcus* infection, an *Escherichia* infection, a *Haemophilius* infection, a *Helicobacter* infection, a *Legionella* infection, a *Leptospira* infection, a *Listeria* infection, a *Mycobacterium* infection, a *Neisseria* infection, a *Porphyromonas* infection, a *Pseudomonus* infection, a *Salmonella* infection, a *Staphylococcus* infection, a *Chlamydia* infection or a combination thereof. The fungal infection may be an *Aspergillus* infection, a *Blastomyces* infection, a *Candida* infection, a Ringworm infection, a Murcormyces infection, or a combination thereof. The parasitic infection may be a *Schistosoma* infection, a *Leishmania* infection, a *Plasmodium* infection, a *Giardia* infection, a *Trypanosoma* infection and a *Taenia* infection.

According to another embodiment, there is provided a compound of the present invention, or pharmaceutically acceptable salt thereof for use in treating a TC-PTP-mediated disease or condition in a patient in need of treatment.

The TC-PTP-mediated disease or condition may be an immunosuppressive disease, and the immunosuppressive disease may be AIDS. The TC-PTP-mediated disease or condition may be a cancer, and the cancer may be prostate cancer, breast cancer, ovarian cancer, multiple myeloma, brain cancer, glioma, lung cancer, salivary cancer, stomach cancer, thymic epitherlial cancer, thyroid cancer, leukemia, melanoma, lymphoma, gastric cancer, pancreatic cancer, kidney cancer, bladder cancer, colon cancer and liver cancer. The TC-PTP-mediated disease or condition may be an infectious disease, and the infectious disease may be a viral infection, a bacterial infection, a fungal infection, a parasitic infection, or a combination thereof. The viral infection may be a cytomegalovirus infection, an Epstein-Barr virus infection, a hepatitis B infection, a hepatitis C virus infection, a herpes virus infection, a human immunodeficiency virus infection, a human T lymphotropic virus infection, a lymphocytic choriomeningitis virus infection, a respiratory syncytial virus infection, rhinovirus infection, or a combination thereof. The bacterial infection may be a *Corynebacterium* infection, an *Enterococcus* infection, an *Escherichia* infection, a *Haemophilius* infection, a *Helicobacter* infection, a *Legionella* infection, a *Leptospira* infection, a *Listeria* infection, a *Mycobacterium* infection, a *Neisseria* infection, a *Porphyromonas* infection, a *Pseudomonus* infection, a *Salmonella* infection, a *Staphylococcus* infection, a *Chlamydia* infection or a combination thereof. The fungal infection may be an *Aspergillus* infection, a *Blastomyces* infection, a *Candida* infection, a Ringworm infection, a Murcormyces infection, or a combination thereof. The parasitic infection may be a *Schistosoma* infection, a *Leishmania* infection, a *Plasmodium* infection, a *Giardia* infection, a *Trypanosoma* infection and a *Taenia* infection.

According to another embodiment, there s provided a nex vivo method of stimulating an isolated antigen-presenting cell comprising:
treating isolated antigen presenting cells with an effective amount of a compound of the present invention, or pharmaceutically acceptable salts thereof, and stereoisomers thereof
wherein the isolated antigen-presenting cell is incubated with an antigen specific to a disease before, during or after the treating the compound,
for a time sufficient to obtain an isolated activated antigen-presenting cell.

According to another embodiment, there is provided an ex vivo method of stimulating an isolated antigen-presenting cell comprising:
treating isolated antigen presenting cells with an effective amount of a compound of Formula II, or pharmaceutically acceptable salts thereof, and stereoisomers thereof:

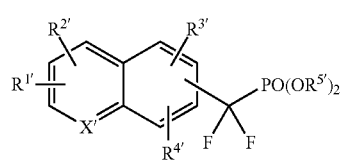

II wherein X' is selected from CH and N;
R$^{1'}$ is selected from the group consisting of (a) C$_{1-3}$alkyl optionally substituted with 1-3 halogens and optionally with one group selected from —OH, —OC$_{1-3}$alkyl optionally substituted with 1-3 halogens, —SO$_x$C$_{1-3}$ alkyl, and —CN, (b) —C(=O)H, (c) —C(=O)C$_{1-3}$ alkyl optionally substituted with 1-3 halogens, (d) —CN, (e) —HC=NOH, (f) —(CH$_3$)C=NOH, (g) —HC=NOC$_{1-3}$alkyl optionally substituted with 1-3 halogens, (h) —(CH$_3$)C=NOC$_{1-3}$alkyl optionally substituted with 1-3 halogens (i) —C(=O)OC$_{1-3}$alkyl optionally substituted with 1-3 halogens, (j) —C(=O)

NHR$^{6'}$, (k) —CH═CH-Phenyl wherein —CH═CH— is optionally substituted with 1-2 substituents independently selected from halogen and C$_{1-2}$alkyl optionally substituted with 1-3 F, (l) —CH$_2$CH$_2$-Phenyl wherein —CH$_2$CH$_2$— is optionally substituted with 1-4 substituents independently selected from halogen and C$_{1-2}$alkyl optionally substituted with 1-3 F, (m) Phenyl, (n) —HET-Phenyl, wherein HET is a 5- or 6-membered heteroaromatic ring containing 1-3 heteroatoms selected from O, N and S, (o) —C≡C-Phenyl, and (p) —CH$_2$-Phenyl, wherein the —CH$_2$— group of —CH$_2$-Phenyl is optionally substituted with 1-2 substituents independently selected from halogen and C$_{1-2}$alkyl optionally substituted with 1-3 F, wherein Phenyl and HET in all occurrences are optionally substituted with 1-3 substituents independently selected from (i) halogen, (ii) —C(═O)OC$_{1-3}$alkyl optionally substituted with 1-3 halogens, (iii) —C(═O)OH (iv) C$_{1-3}$alkyl optionally substituted with 1-3 halogens, (v) —OC$_{1-3}$alkyl optionally substituted with 1-3 halogens, (vi) —SO$_x$Me, and (vii) —SO$_2$NH$_2$;

R$^{6'}$ is selected from the group consisting of H, C$_{1-3}$alkyl optionally substituted with 1-3 halogens, Phenyl, and —CH$_2$-Phenyl, wherein Phenyl in both occurrences is optionally substituted with 1-3 substituents independently selected from (i) halogen, (ii) —C(═O)OC$_{1-3}$alkyl optionally substituted with 1-3 halogens, (iii) —C(═O)OH (iv) C$_{1-3}$alkyl optionally substituted with 1-3 halogens, and (v) —OC$_{1-3}$alkyl optionally substituted with 1-3 halogens;

R$^{2'}$ and R$^{4'}$ are independently selected from H, halogen, —CH$_3$, —CF$_3$, —OCH$_3$, and —OCF$_3$;

R$^{3'}$ is halogen, wherein the halogen is bonded to the fused aromatic ring of Formula II at a position ortho to the —CF$_2$PO(OR$^{5'}$)$_2$ group, each R$^{5'}$ group is independently selected from the group consisting of H and C$_{1-3}$alkyl optionally substituted with 1-3 halogens, and x is 0, 1, or 2;

wherein the isolated antigen-presenting cell is incubated with an antigen specific to a disease before, during of after the treating with the compound of Formula II for a time sufficient to obtain an isolated activated antigen-presenting cell.

According to another embodiment, there is provided an ex vivo method of stimulating an isolated antigen-presenting cell comprising:

treating isolated antigen presenting cells with an effective amount of at least one of an effective amount of compound of the present invention an effective amount of a compound of Formula II of pharmaceutically acceptable salts thereof, and stereoisomers thereof:

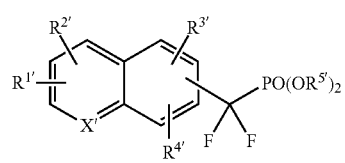

wherein X' is selected from CH and N;

R$^{1'}$ is selected from the group consisting of (a) C$_{1-3}$alkyl optionally substituted with 1-3 halogens and optionally substituted with one group selected from —OH, —OC$_{1-3}$alkyl optionally substituted with 1-3 halogens, —SO$_x$C$_{1-3}$alkyl, and —CN, (b) —C(═O)H, (c) —C(═O)C$_{1-3}$alkyl optionally substituted with 1-3 halogens, (d) —CN, (e) —HC═NOH, (f) —(CH$_3$)C═NOH, (g) —HC═NOC$_{1-3}$alkyl optionally substituted with 1-3 halogens, (h) —(CH$_3$)C═NOC$_{1-3}$alkyl optionally substituted with 1-3 halogens (i) —C(═O)OC$_{1-3}$alkyl optionally substituted with 1-3 halogens, (j) —C(═O)NHR$^{6'}$, (k) —CH═CH-Phenyl wherein —CH═CH— is optionally substituted with 1-2 substituents independently selected from halogen and C$_{1-2}$alkyl optionally substituted with 1-3 F, (l) —CH$_2$CH$_2$-Phenyl wherein —CH$_2$CH$_2$— is optionally substituted with 1-4 substituents independently selected from halogen and C$_{1-2}$alkyl optionally substituted with 1-3 F, (m) Phenyl, (n) —HET-Phenyl, wherein HET is a 5- or 6-membered heteroaromatic ring containing 1-3 heteroatoms selected from O, N and S, (o) —C≡C-Phenyl, and (p) —CH$_2$-Phenyl, wherein the —CH$_2$— group of —CH$_2$-Phenyl is optionally substituted with 1-2 substituents independently selected from halogen and C$_{1-2}$alkyl optionally substituted with 1-3 F, wherein Phenyl and HET in all occurrences are optionally substituted with 1-3 substituents independently selected from (i) halogen, (ii) —C(═O)OC$_{1-3}$alkyl optionally substituted with 1-3 halogens, (iii) —C(═O)OH (iv) C$_{1-3}$alkyl optionally substituted with 1-3 halogens, (v) —OC$_{1-3}$alkyl optionally substituted with 1-3 halogens, (vi) —SO$_x$Me, and (vii) —SO$_2$NH$_2$;

R$^{6'}$ is selected from the group consisting of H, C$_{1-3}$alkyl optional substituted with 1-3 halogens, Phenyl, and —CH$_2$-Phenyl, wherein Phenyl in both occurrences is optionally substituted with 1-3 substituents independently selected from (i) halogen (ii) —C(═O)OC$_{1-3}$alkyl optionally substituted with 1-3 halogens, (iii) —C(═O)OH (iv) C$_{1-3}$alkyl optionally substituted with 1-3 halogens, and (v) —OC$_{1-3}$alkyl optionally substituted with 1-3 halogens;

R$^{2'}$ and R$^{4'}$ are independently selected from H, halogen, —CH$_3$, —CF$_3$, —OCH$_3$, and —OCF$_3$:

R$^{3'}$ is halogen, wherein the halogen is bonded to the fused aromatic ring of Formula II at a position ortho to the —CF$_2$PO(OR$^{5'}$)$_2$ group.

each R$^{5'}$ group is independently selected from the group consisting of H and C$_{1-3}$alkyl optionally substituted with 1-3 halogens, and x is 0, 1, or 2; and combinations thereof;

wherein the antigen-presenting cell is incubated with an antigen specific to a disease before, during or after the contacting with at least of one the compound of any one of claims 1 to 7 and Formula II; for a time sufficient to obtain an isolated activated antigen-presenting cell.

According to another embodiment, there is provided a method for improving or treating a disease in a patient in need thereof comprising:

administering an isolated activated antigen presenting cell obtained by the method of the present invention to the patient.

wherein the disease causes expression of the antigen specific to a disease in the patient.

The isolated antigen presenting cell or the isolated activated antigen presenting cell may be a dendritic cell. The isolated antigen presenting cell or the isolated activated antigen presenting cell are from the same patient.

The treating of the isolated antigen presenting cells comprises a maturation cocktail.

The treating of the isolated antigen presenting cells further comprises a maturation cocktail.

The maturation cocktail comprises LPS, MPLA, INFγ, CD40L, IL-1β, IL-6, TNF-α, PGE-2, or combinations thereof.

The maturation cocktail may be at least one of the following cocktails:
a) LPS and INFγ;
b) MPLA and INFγ;
c) CD40L and INFγ;
d) IL-1β, IL-6 and TNF-α; and
e) IL-1β, IL-6, TNF-α and PGE-2.

The disease may be an immunosuppressive disease, and the immunosuppressive disease may be AIDS. The disease may be a cancer, and the cancer may be prostate cancer, breast cancer, ovarian cancer, multiple myeloma, brain cancer, glioma, lung cancer, salivary cancer, stomach cancer, thymic epitherlial cancer, thyroid cancer, leukemia, melanoma, lymphoma, gastric cancer, pancreatic cancer, kidney cancer, bladder cancer, colon cancer and liver cancer. The disease may be an infectious disease, and the infectious disease may be a viral infection, a bacterial infection, a fungal infection, a parasitic infection, or a combination thereof. The viral infection may be a cytomegalovirus infection, an Epstein-Barr virus infection, a hepatitis B infection, a hepatitis C virus infection, a herpes virus infection, a human immunodeficiency virus infection, a human T lymphotropic virus infection, a lymphocytic choriomeningitis virus infection, a respiratory syncytial virus infection, rhinovirus infection, or a combination thereof. The bacterial infection may be a *Corynebacterium* infection, an *Enterococcus* infection, an *Escherichia* infection, a *Haemophilius* infection, a *Helicobacter* infection, a *Legionella* infection, a *Leptospira* infection a *Listeria* infection, a *Mycobacterium* infection, a *Neisseria* infection, a *Porphyromonas* infection, a *Pseudomonus* infection, a *Salmonella* infection, a *Staphylococcus* infection, a *Chlamydia* infection or a combination thereof. The fungal infection may be an *Aspergillus* infection, a *Blastomyces* infection, a *Candida* infection, a Ringworm infection, a Murcormyces infection, or a combination thereof. The parasitic infection may be a *Schistosoma* infection, a *Leishmania* infection, a *Plasmodium* infection, a *Giardia* infection, a *Trypanosoma* infection and a *Taenia* infection.

The isolated activated antigen presenting cell may be administered into the bloodstream of the patient, into a lymph node of the patient, into tumor of the patient, into a tissue of the patient, and combinations thereof.

According to another embodiment, there is provided a method of preventing or treating a TC-PTP mediated disease or condition in a patient in need of treatment comprising administering a therapeutically effective amount of a compound of the present invention, or a pharmaceutically acceptable salt thereof to the patient.

The TC-PTP-mediated disease or condition may be an immunosuppressive disease, and the immunosuppressive disease may be AIDS. The TC-PTP-mediated disease or condition may be a cancer and the cancer may be prostate cancer, breast cancer, ovarian cancer, multiple myeloma, brain cancer, glioma, lung cancer, salivary cancer, stomach cancer, thymic epitherlial cancer, thyroid cancer, leukemia, melanoma, lymphoma, gastric cancer, pancreatic cancer, kidney cancer, bladder cancer, colon cancer and liver cancer. The TC-PTP-mediated diseases or conditions may be an infectious disease, and the infectious disease may be a viral infection, a bacterial infection, a fungal infection, a parasitic infection, or a combination thereof. The viral infection may be a cytomegalovirus infection, an Epstein-Barr virus infection, a hepatitis B infection, a hepatitis C virus infection, a herpes virus infection a human immunodeficiency virus infection, a human T lymphotropic virus infection, a lymphocytic choriomeningitis virus infection, a respiratory syncytial virus infection, rhinovirus infection, or a combination thereof. The bacterial infection may be a *Corynebacterium* infection, an *Enterococcus* infection, an *Escherichia* infection, a *Haemophilius* infection, a *Helicobacter* infection, a *Legionella* infection, a *Leptospira* infection, a *Listeria* infection, a *Mycobacterium* infection, a *Neisseria* infection, a *Porphyromonas* infection, a *Pseudomonus* infection, a *Salmonella* infection, a *Staphylococcus* infection, a *Chlamydia* infection or a combination thereof. The fungal infection may be an *Aspergillus* infection, a *Blastomyces* infection, a *Candida* infection, a Ringworm infection, a Murcormyces infection, or a combination thereof. The parasitic infection may be a *Schistosoma* infection, a *Leishmania* infection, a *Plasmodium* infection, a *Giardia* infection, a *Trypanosoma* infection and a *Taenia* infection.

The administration may be oral administration, intravenous administration, subcutaneous administration, sublingual administration, inhalation administration or intramuscular administration, or a combination thereof.

According to another embodiment, there is provided a pharmaceutical composition comprising
(1) a first compound of present invention or a pharmaceutically acceptable salt thereof;
(2) one or more additional compounds selected from the group consisting of:
   (a) a cytotoxic agent;
   (b) an antimetabolite;
   (c) an alkylating agent;
   (d) an anthracycline;
   (e) an antibiotic;
   (f) an anti-mitotic, agent;
   (g) an hormone therapy;
   (h) a signal transduction inhibitor;
   (i) a gene expression modulator;
   (j) an apoptosis inducer;
   (k) anangiogenesis inhibitor
   (l) an immunotherapy agent
and
(3) a pharmaceutically acceptable carrier.

The cytotoxic agent may be taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, analogs or homologs thereof, or a combination thereof.

The antimetabolites may be methotrexate, 6-mercaptopurine, 6-thioguanine, cytarabine, 5-fluorouracil decarbazine, or a combination thereof.

The alkylating agent may be mechlorethamine, thioepa chlorambucil, melphalan, carmustine (BSNU), lomustine (CCNU), cyclothosphamide, busulfan, dibromomannitol, streptozotocin, mitomycin C, cis-dichlorodiamine platinum (II) (DDP) cisplatin, or a combination thereof.

The anthracycline may be daunorubicin, doxorubicin or a in combination thereof.

The antibiotic may be dactinomycin, bleomycin, mithramycin, anthramycin (AMC), or a combination thereof.

The anti-mitotic agent may be vincristine, vinblastine, or a combination thereof.

The signal transduction inhibitor may be imatinib, trastuzumab, or a combination thereof.

The gene expression modulator may be a siRNA, a shRNA, an antisense oligonucleotide, an HDAC inhibitor, or a combination thereof.

The immunotherapy agent may be a monoclonal antibody, a chimeric antigen receptors (CARs)-T-Cell, or a combination thereof.

The hormone therapy may be an luteinizing hormone-releasing hormone (LHRH) antagonist.

The apoptosis inducers may be a recombinant human TNF-related apoptosis-inducing ligand (TRAIL).

The angiogenesis inhibitors may be sorafenib, sunitinib, pazopanib, everolimus or a combination thereof.

The monoclonal antibody may be anti-CTLA4, or a combination thereof.

The first compound may be

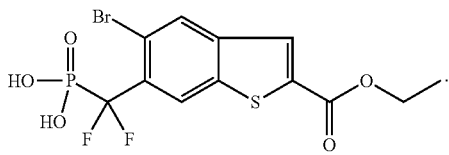 [SMILES: CCOC(=O)c1cc2cc(Br)c(C(F)(F)P(=O)(O)O)cc2s1]

The present invention relates to compounds of structural Formula I along with their pharmaceutically acceptable salts:

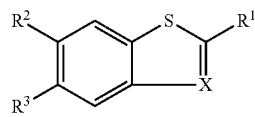

These compounds are inhibitors of TC-PTP and are useful for activating antigen presenting cells for treatment of diseases where the patient is unable to mount a sufficient immune response. Such compounds may be useful in the treatment of cancer, AIDS and related medical conditions, infectious diseases and may also be useful in the treatment of other TC-PTP-mediated diseases or conditions.

The present invention also relates to the direct administration of a compound of the present invention to a patient in need of such treatment, using oral, intravenous, subcutaneous, sublingual, inhalation or intramuscular administration.

The present invention also relates to methods for ex vivo treatment of cells harvested from a patient with compounds of the present invention in a suitable medium in order to make those cells suitable for injection into a patient.

The present invention also relates to methods for ex vivo treatment of antigen-presenting cells (such as dendritic cells) with compounds of the present invention in combination with a therapeutically effective amount of an antigen known to be useful to create a desired change in those cells.

The present invention also relates to the use of biological agents that reduce the amount of TC-PTP activity in antigen-presenting cells (such dendritic cells) during the ex vivo maturation of such cells. Such agents include siRNA, CRSPR/CAs9, talens, zinc finger nucleases, shRNA, and antisense oligonucleotides that recognize the PTPN2 gene sequence.

The present invention also relates to methods for the treatment or control of cancer, infectious diseases such as viral infections, bacterial infections, fungal infections and parasitic infections, and related medical conditions by injecting activated dendritic cells into a patient wherein the dendritic cells have been manipulated to present antigens particular to the disease from which the patient is suffering.

The present invention covers administration of activated dendritic cells to a patient in need of such therapy by injecting such cells into the bloodstream, into a lymph node, directly into a tumor, or directly into another tissue that has been impacted by the disease the patient is being treated for.

Types of cancer that may be treated by the present invention include, but are not limited to, prostate cancer, breast cancer, ovarian cancer, multiple myeloma, brain cancer, glioma, lung cancer, salivary cancer, stomach cancer, thymic epitherlial cancer, thyroid cancer leukemia, melanoma, lymphoma, gastric cancer, pancreatic cancer, kidney cancer, bladder cancer, colon cancer and liver cancer.

Types of infectious disease that may be treated by the present invention include, but are not limited to those caused by the following viruses, bacteria and parasites, cytomegalovirus Epstein-Barr virus, hepatitis B, hepatitis C virus, herpes virus, human immunodeficiency virus, human T lymphotropic virus, lymphocytic choriomeningitis virus, respiratory syncytial virus, and/or rhinovirus; *Corynebacterium, Enterococcus, Escherichia, Haemophilius, Helicobacter, Legionella, Leptospira, Listeria, Mycobacterium, Neisseria, Porphyromonas, Pseudomonus, Salmonella, Staphylococcus* and *Chlamydia*; or *Schistosoma, Leishmania, Plasmodium, Giardia, Trypanosoma* and *Taenia*, or fungi infections such as infections caused by *Aspergillus, Blastomyces, Candida*, Ringworm, and Murcormyces.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
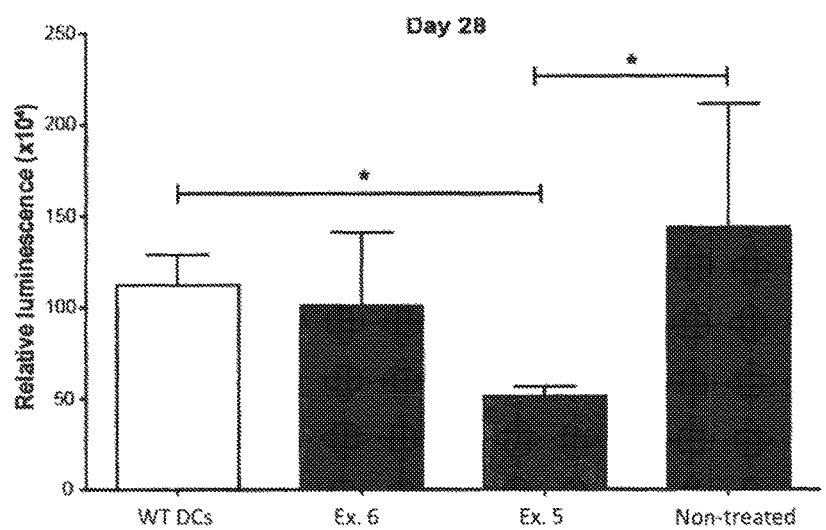
FIG. 1 illustrates the tumor volume in mice 28 days following a single treatment of mature dendritic cells activated by either the compound of Example 6 or Example 5.

The present invention relates to compounds of structural Formula I along with their pharmaceutically acceptable salts and stereoisomers thereof:

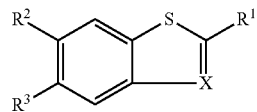

wherein

X is selected from CH and N;

$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (b) —(C=O)$R^4$; (c) —CN; (d) —(C=O)$OR^4$; (e) —(C=O)$NHR^4$; (f) —(C=O)$NR^5R^6$; and (g) aryl or heteroaryl wherein the aryl and hetero aryl group itself may be optionally substituted with 1-3 substituents independently selected from (i) halogen, (ii) —(C=O)$OC_{1-3}$ alkyl optionally substituted with 1-3 halogens, (iii) —COOH (iv) $C_{1-3}$ alkyl optionally substituted with 1-3 halogens, (v) —$OC_{1-3}$ alkyl optionally substituted with 1-3 halogens, (vi) —$SO_x$Me, (vii) —CN, and (viii) —$SO_2NH_2$;

$R^2$ and $R^3$ are independently selected from the group consisting of (a) halogen; (b) difluoromethylphosphonic acid;

$R^4$ is selected from the group consisting of (a) H; (b) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (d) aryl or heteroaryl wherein the aryl or heteroaryl group itself may be optionally substituted by 1-3 halogens, $C_{1-3}$ alkyl or $C_{1-3}$ haloalkyl;

$R^5$ and $R^6$ are independently selected from the group consisting of (a) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (b) aryl or heteroaryl wherein the aryl or heteroaryl group itself may be optionally substituted by 1-3 halogens, $C_{1-3}$ alkyl or $C_{1-3}$ haloalkyl;

$R^5$ and $R^6$, together with the nitrogen atom to which they are attached may be joined to form a 5- to 7-membered ring, which may be substituted with a 1-3 groups independently selected from (i) halogen, (ii) —(C=O)$OC_{1-3}$ alkyl, (iii) —(C=O)OH (iv) $C_{1-3}$ alkyl optionally substituted with 1-3 halogens, (v) —$OC_{1-3}$ alkyl optionally substituted with 1-3 halogens, (vi) —OH, (vii) $C_{1-3}$ hydroxyalkyl, (viii) aryl or heteroaryl wherein the aryl or heteroaryl group itself may be optionally substituted by 1-3 halogens, $C_{1-3}$ alkyl or $C_{1-3}$ haloalkyl;

x is an integer from 0 to 2.

According to another embodiment, the current invention can be summarized by structural Formula Ia:

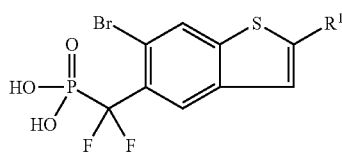

Ia and pharmaceutically acceptable salts and stereoisomers thereof, wherein:

$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, and —CN; (b) —(C=O)$R^4$; (c) —CN; (d) —(C=O)$OR^4$; (e) —(C=O)$NHR^4$; and (f) —(C=O)$NR^5R^6$;

$R^4$ is selected from the group consisting of (a) H; and (b) $C_{1-3}$ alkyl optionally substituted with 1-5 halogens;

$R^5$ and $R^6$ are independently selected from the group consisting of $C_{1-3}$ alkyl optionally substituted with 1-5 halogens and optionally with one group selected from —OH, and —$OC_{1-3}$ alkyl optionally substituted with 1-3 halogens;

$R^5$ and $R^6$, together with the nitrogen atom to which they are attached may be joined to form a 5- to 7-membered ring, which may be substituted with a 1-3 groups independently selected from (i) halogen, (ii) $C_{1-3}$ alkyl optionally substituted with 1-3 halogens, (iii) —$OC_{1-3}$ alkyl optionally substituted with 1-3 halogens, (iv) —OH, and (vii) $C_{1-3}$ hydroxyalkyl;

According to yet another embodiment, the current invention can be summarized by structural Formula Ib:

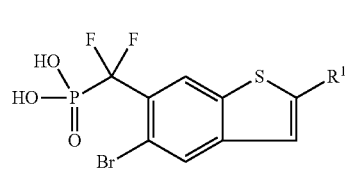

Ib and pharmaceutically acceptable salts and stereoisomers thereof, wherein:

$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, and —CN; (b) —(C=O)$R^4$; (c) —CN; (d) —(C=O)$OR^4$; (e) —(C=O)$NHR^4$; and (f) —(C=O)$NR^5R^6$;

$R^4$ is selected from the group consisting of (a) H; and (b) $C_{1-3}$ alkyl optionally substituted with 1-5 halogens;

$R^5$ and $R^6$ are independently selected from the group consisting of $C_{1-3}$ alkyl optionally substituted with 1-5 halogens and optionally with one group selected from —OH, and —$OC_{1-3}$ alkyl optionally substituted with 1-3 halogens;

$R^5$ and $R^6$, together with the nitrogen atom to which they are attached may be joined to form a 5 to 7-membered ring, which may be substituted with a 1-3 groups independently selected from (i) halogen, (ii) $C_{1-3}$ alkyl optionally substituted with 1-3 halogens, (iii) —$OC_{1-3}$ alkyl optionally substituted with 1-3 halogens, (iv) —OH, and (vii) $C_{1-3}$ hydroxyalkyl;

The invention includes the compounds as shown, and also includes (where possible) individual diastereomers, enantiomers, and epimers of the compounds, and mixtures of diastereomers and/or enantiomers thereof including racemic mixtures. Although the specific stereochemistries disclosed herein are preferred, other stereoisomers, including diastereomers, enantiomers, epimers, and mixtures of these may also be useful in activating APCs. Inactive or less active diastereoisomers and enantiomers are useful for scientific studies relating to the enzyme target and the mechanism of activation.

The compounds disclosed herein may be used in pharmaceutical compositions comprising (a) the compound(s) or pharmaceutically acceptable salts thereof, and (b) a pharmaceutically acceptable carrier. The compounds may be used in pharmaceutical compositions that include one or more other active pharmaceutical ingredients. The compounds may also be used in pharmaceutical compositions in which the compound of Formula I or a pharmaceutically acceptable salt thereof is the only active ingredient.

According to an embodiment, the compounds of the present invention are inhibitors of TC-PTP and are useful for activating antigen presenting cells for treatment of diseases where the patient is unable to mount a sufficient immune response. Such compounds may be useful in the treatment of cancer, viral infections, bacterial infections, fungal infections and parasitic infections, and may also be useful in the treatment of other TC-PTP-mediated diseases or conditions.

According to another embodiment, the compounds of the present invention may be given directly to a patient in need of such treatment, using oral, intravenous, subcutaneous, sublingual, inhalation or intramuscular administration.

According to another embodiment, the present invention also relates to methods for ex vivo treatment of cells harvested from a patient with compounds of the present invention in a suitable medium in order to make those cells suitable for injection into a patient.

According to another embodiment, the present invention also relates to methods for ex vivo treatment of antigen-presenting cells (such as dendrite cells—DC) with compounds of the present invention in combination with a therapeutically effective amount of an antigen known to be useful to create a desired change in those cells.

According to another embodiment, the present invention also relates to methods for ex vivo treatment of antigen-presenting cells (such as dendrite cells) with compounds of the present invention in combination with a suitable maturation cocktail that may consist of, but is not limited to, one or more of the following agents:
a) LPS and INFγ;
b) MPLA and INFγ;
c) CD40L and INFγ;
d) IL-1β, IL-6 and TNF-α;
e) IL-1β, IL-6, TNF-α and PGE-2;

According to another embodiment, the present invention also relates to methods for the treatment or control of cancer, and infectious diseases such as viral infections, bacterial infections, fungal infections and parasitic infections and related medical conditions by injecting activated dendritic cells into a patient wherein the dendritic cells have been manipulated to present antigens particular to the disease from which the patient is suffering.

According to an embodiment, it is believed that for an activated DC to have utility in treatment of cancer, it must be exposed to a tumor-specific antigen during the maturation process which it then takes up and presents on the cell surface. Similarly, it is believed that if the activated DC is exposed to an antigen specific to an infectious agent, the DCs may have utility in the treatment of the associated infectious disease. (Moll, 2004).

According to another embodiment, the present invention relates to the administration of activated dendritic cells to a patient in need of such therapy by injecting such cells into the bloodstream, into a lymph node, directly into a tumor, or directly into another tissue that has been impacted by the disease the patient is being treated for.

Types of cancer that may be treated by compounds of the present invention include, but are not limited to, prostate cancer, breast cancer, brain cancer, glioma, lung cancer, salivary cancer, stomach cancer, thymic epithelial cancer, thyroid cancer, ovarian cancer, multiple myeloma, leukemia, melanoma, lymphoma, gastric cancer, kidney cancer, pancreatic cancer, bladder cancer, colon cancer and liver cancer.

Types of viral infections that may be treated by the present invention include, but are not limited to, infections caused by cytomegalovirus Epstein-Barr virus, hepatitis B, hepatitis C virus, herpes virus, human immunodeficiency virus, human lymphotropic virus, lymphocytic choriomeningitis virus, respiratory syncytial virus and/or rhinovirus.

Types of bacterial infections that may be treated by the present invention include, but are not limited to, infections caused by *Corynebacterium, Enterococcus, Escherichia, Haemophilius, Helicobacter, Legionella, Leptospira, Listeria, Mycobacterium, Neisseria, Porphyromonas, Pseudomonus, Salmonella, Staphylococcus* and *Chlamydia*.

Types of parasitic infections that may be treated by the present invention include, but are not limited to, infections caused by *Schistosoma, Leishmania, Plasmodium, Giardia, Trypanosoma* and *Taenia*.

Types of fungi infections that may be treated by the present invention include, but are not limited to, infections caused by *Aspergillus, Blastomyces, Candida*, Ringworm, and Murcormyces.

According to yet another embodiment, the invention also includes in vitro treatment of primary cells with a compound of Formula I, Formula Ia, and/or Formula Ib or a pharmaceutically acceptable salt thereof, along with incubation with a suitable antigen in order to produce activated cells suitable for therapeutic treatment of a patient in need of immunotherapy.

Abbreviations

Abbreviations an terms that are commonly used in the fields of organic chemistry, medicinal chemistry, pharmacology, and medicine and are well known to practitioners in these fields are used herein. Representative abbreviations and definitions are provided below:

Ac is acetyl [$CH_3C(O)$—], $Ac_2O$ is acetic anhydride; APC is antigen-presenting cell; 9-BBN is 9-borabicyclo[3.3.1] nonane; Bn is benzyl; BOC is tert Butyloxycarbonyl; DIAD is diisopropylazodicarboxylate; DIBAL is diisobutylaluminum hydride; DMF N,N-dimethylformamide; DMSO is dimethyl sulfoxide; EDAC (or EDC) is 1-ethyl-[3-(dimethylamino)propyl]-carbodiimide HCl; $Et_3N$ is triethylamine; Et is ethyl; EtOAc is ethyl acetate; EtOH is ethanol; 3-F-Ph is 3-fluorophenyl, HCl is hydrochloric acid; HOBt is 1-hydroxybenzotriazole; HPLC is high performance liquid chromatography; LCMS is HPLC with mass Spectral detection; LG is leaving group; M is molar; mmol is millimole; Me is methyl; MeOH is methanol; MsCl is methanesulfonyl chloride; N is normal; NaHMDS is sodium hexamethyldisiliazide, NaOAc is sodium acetate; NaOtBu is sodium tert-butoxide; NMO is N-methylmorpholine N oxide; NMP is N Methyl pyrrolidinone; $Pd(dba)_2$ is tris(dibenzylideneacetone)dipalladium; $PdCl_2(Ph_3P)_2$ is dichlorobis-(triphenylphosphene) palladium; PG Denotes an unspecified protecting group; Ph is phenyl; PhMe is toluene; $PPh_3$ is triphenylphosphine; PMB is para-methoxybenzyl; RT is room temperature; TBAF is tetrabutyl ammonium fluoride; TBS is tert-butyldimethylsilyl; tBu is tert-butyl; Tf is triflate; TFA is trifluoroacetic acid; THF is tetrahydrofuran; TLC is thin layer chromatography; TMS is trimethylsilyl; TPAP is tetrapropylammonium perruthenate.

Definitions

"Alkyl", as well as other groups having the prefix "alk", such a alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from C3-10, the term alkyl also includes cycloalkyl groups, and combinations of linear or branched alkyl chains combined with cycloalkyl structures. When no number of carbon atoms is specified, C1-6 is intended.

"Cycloalkyl" is a subset of alkyl and means a saturated carbocyclic ring having a specified number of carbon atoms.

Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., C1-6 alkoxy), or any number within this range [i.e., methoxy (MeO—), ethoxy, isopropoxy, etc.].

The term "alkylthio" refers to straight or branched chain alkylsulfides of the number of carbon atoms specified (e.g., C1-6 alkylthio), or any number within this range [i.e. methylthio (MeS—), ethylthio, isopropylthio, etc.].

The term "alkylamino" refers to straight or branched alkylamines of the number of carbon atoms specified (e.g., C1-6 alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., C1-6 alkylsulfonyl), or any number within this range [i.e., methylsulfonyl ($MeSO_2^-$), ethylsulfonyl, isopropylsulfonyl, etc.].

The term "alkylsulfinyl" refers to straight or branched chain alkylsulfones of the number of carbon atoms specified (e.g., $C_{1-6}$alkylsulfinyl), or any number within this range [i.e., methylsulfinyl (MeSO—), ethylsulfinyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl ($MeOCO^-$), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 14-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, 2-oxopiperidin-1-yl, 2-oxopyrrolidin-1-yl, 2-oxoazetidin-1-yl, 1,2,4-oxadiazin-5(6H)-one-3-yl, and the like.

"Heteroaryl" means an aromatic or partially aromatic heterocycle that contains a least one ring heteroatom selected from O, S and N. Heteroaryls thus include heteroaryls fused to other kinds of rings, such as aryls, cycloalkyls and heterocycles that are not aromatic. Examples of heteroaryl groups include; pyrrolyl, isoxazolyl, isothiazolyl, pyrazolyl, pyridyl, oxazolyl, oxadiazolyl (in particular, 1,3, 4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The term «composition» as used herein is intended to encompass a product comprising the specified ingredients in the specified amounts, as well as any product which results, directly or indirectly, from combination of the specified ingredients in the specified amounts. Such term in relation to pharmaceutical composition is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" or "acceptable" it is meant the carrier, diluent or excipient must be compatible with the other ingredients of the formulation and not deleterious to the recipient thereof.

Compounds of structural Formula I, structural Formula Ia and/or structural Formula Ib may contain one or more asymmetric centers and can thus occur as racemates and racemic mixtures, single enantiomers, diastereomeric mixtures and individual diastereomers. The present invention is meant to comprehend all such isomeric forms of the compounds of structural Formula I, structural Formula Ia and/or structural Formula Ib.

Compounds of structural Formula I, structural Formula Ia and/or structural Formula Ib may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural Formula I, structural Formula Ia and/or structural Formula Ib may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of generic Formula I, Formula Ia and/or Formula Ib, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I, Formula Ia and/or Formula Ib. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I, Formula Ia and/or Formula Ib can be prepared without undue experimentation by conventional techniques well known to those skilled in the art or by processes analogous to those described in the Schemes and Examples herein using appropriate isotopically enriched reagents and/or intermediates.

Salts and Formulations

It will be understood that, as used herein, references to the compounds of structural Formula I, Formula Ia and/or Formula Ib are meant to also include the pharmaceutically acceptable salts, and also salts that are not pharmaceutically acceptable when they are used as precursors to the free compounds or their pharmaceutically acceptable salts or in other synthetic manipulations. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, furnarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl benzoyl, and aminoacyl, can be employed. Included are those esters and acyl groups known in the art for modifying the solubility hydrolysis characteristics for use as sustained-release or prodrug formulations.

Solvates, in particular hydrates, of the compounds of structural Formula I, Formula Ia and/or Formula Ib are included in the present invention as well.

According to an embodiment, the compounds of structural Formula I, Formula Ia and/or Formula Ib may be included in various formulations for use as medicaments. Formulations for oral use may be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethy-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the know art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an I atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebuliser contains a solution or pension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from log to 20 mg of the compound of the invention per actuation and the actuation volume may vary from 11 to 1001. A typical formulation may comprise a compound of formula I, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-controlled-, targeted and programmed release.

In the case dry powder inhalers and aerosols, the dosage unit is determined by means of a valve which delivers a metered amount. Units in accordance with the invention are typically arranged to administer a metered dose or "puff" containing from 1 fig to 10 mg of the compound of formula I. The overall daily dose will typically be in the range 1 lag to 10 mg which may be administered in a single dose or, more usually, as divided doses throughout the day.

Compounds of Formula Ia and/or Formula Ib may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Utilities

The compounds specifically exemplified herein exhibit good efficacy in inhibiting the TC-PTP enzyme, as shown by their in vitro assays. The compounds generally have an $IC_{50}$ value of less than 10 μM in the enzyme assay described in the Assays section, and preferably have an $IC_{50}$ value of less than 1 μM.

According to an embodiment, the inhibitors of TC-PTP may improve and may have utility in preventing or treating immunosuppressive diseases.

One aspect of the invention provides a method for the treatment and control of cancer, which comprises administering to a patient in need of such treatment a therapeutically effective amount of dendritic cells that have been activated by treatment with a compound of Formula I, Formula Ia and/or Formula Ib, and/or compounds of Formula II and an antigen or mixture of antigens derived from the cancer cells affecting the patient.

A second aspect of the invention provides a method for the treatment and control of HIV infection, which comprises administering to a patient in need of such treatment a therapeutically effective amount of dendritic cells that have been activated by treatment with a compound of Formula I, Formula Ia and/or Formula Ib, and/or compounds of Formula II and an antigen or mixture of antigens derived specific to the HIV virus.

A third aspect of the invention provides a method for the treatment and control of immunosuppressive diseases, which comprises administering to a patient in need of such treatment a therapeutically effective amount of dendritic cells that have been activated by treatment with a compound of Formula I, Formula Ia and/or Formula Ib, and/or compounds of Formula II and an antigen or mixture of antigens derived from cells affected by the immunosuppressive diseases.

The compounds of Formula II are inhibitors of TC-PTP having the general formula:

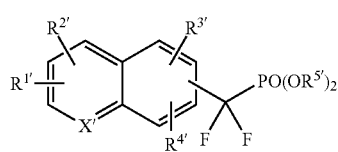

II pharmaceutically acceptable salts thereof, and stereoisomers thereof
wherein
X' is selected from CH and N;
$R^{1'}$ is selected from the group consisting of (a) $C_{1-3}$alkyl optionally substituted with 1-3 halogens and optionally with one group selected from —OH, —$OC_{1-3}$alkyl optionally substituted with 1-3 halogens, —$SO_xC_{1-3}$alkyl, and —CN, (b) —C(=O)H, (c) —C(=O)$C_{1-3}$alkyl optionally substituted with 1-3 halogens, (d) —CN, (e) —HC=NOH, (f) —(CH$_3$)C=NOH, (g) —HC=NO$C_{1-3}$alkyl optionally substituted with 1-3 halogens, (h) —(CH$_3$)C=NO$C_{1-3}$alkyl optionally substituted with 1-3 halogens (i) —C(=O)O$C_{1-3}$alkyl optionally substituted with 1-3 halogens, (j) —C(=O)NHR$^{6'}$, (k) —CH=CH-Phenyl wherein —CH=CH— is optionally substituted with 1-2 substituents independently selected from halogen and $C_{1-2}$alkyl optionally substituted with 1-3 F, (l) —CH$_2$CH$_2$-Phenyl wherein —CH$_2$CH$_2$— is optionally substituted with 1-4 substituents independently selected from halogen and $C_{1-2}$alkyl optionally substituted with 1-3 F, (m) Phenyl, (n) —HET-Phenyl, wherein HET is a 5- or 6-membered heteroaromatic ring containing 1-3 heteroatoms selected from O, N and S, (o) —C≡C-Phenyl, and (p) —CH$_2$-Phenyl, wherein the —CH$_2$— group of —CH$_2$-Phenyl is optionally substituted with 1-2 substituents independently selected from halogen and $C_{1-2}$alkyl optionally substituted with 1-3 F, wherein Phenyl and HET in all occurrences are optionally substituted with 1-3 substituents independently selected from (i) halogen, (ii) —C(=O)O$C_{1-3}$alkyl optionally substituted with 1-3 halogens, (iii) —C(=O)OH (iv) $C_{1-3}$alkyl optionally substituted with 1-3 halogens, (v) —O$C_{1-3}$alkyl optionally substituted with 1-3 halogens, (vi) —$SO_x$Me, and (vii) —SO$_2$NH$_2$;
$R^{6'}$ is selected from the group consisting of H, $C_{1-3}$alkyl optionally substituted with 1-3 halogens, Phenyl, and —CH$_2$-Phenyl, wherein Phenyl in both occurrences is optionally substituted with 1-3 substituents independently selected from (i) halogen, (ii) —C(=O)O$C_{1-3}$alkyl optionally substituted with 1-3 halogens, (iii) —C(=O)OH, (iv) $C_{1-3}$alkyl optionally substituted with 1-3 halogens, and (v) —O$C_{1-3}$alkyl optionally substituted with 1-3 halogens;
$R^{2'}$ and $R^{4'}$ are independently selected from H, halogen, —CH$_3$, —CF$_3$, —OCH$_3$, and —OCF$_3$;
$R^{3'}$ is halogen, wherein said halogen is bonded to the fused aromatic ring of Formula II at a position ortho to the —CF$_2$PO(OR$^{5'}$)$_2$ group,
each $R^{5'}$ group is independently selected from the group consisting of H and $C_{1-3}$alkyl optionally substituted with 1-3 halogens, and
x is 0, 1, or 2.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g., chickens).

Optimal Concentration

The effective concentration of a compound of Formula I for use in activating APCs may be determined through an in vitro titration of the compound in cells and monitoring the release of IL-12. The lowest concentration that provides maximal release of IL-12 in the absence of cellular toxicity will be dependent on the compound's intrinsic potency and its ability to inhibit TC-PTP in the cell. This optimal concentration is then used to treat ACPs for activation of antigen presentation. Useful concentrations range from 1 nM to 1 mM in aqueous buffer or cell media. Preferably, the concentration used is between 1 μM and 100 μM.

For in vitro use, the compounds of Formula I, Formula Ia and/or Formula Ib can be administered as a solution in water, DMSO or a mixture of water and DMSO, to a suspension of APCs in a typical media such that the final concentration is about 1 nM to about 500 μM.

For in vivo use, dosage levels of the order of from about 0.01 mg to about 140 mg/kg of body weight per day are useful in the treatment of the above-indicated conditions, or alternatively about 0.5 mg to about 7 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg 500 mg, 600 mg, 800 mg, or 1000 mg.

Kits

Compounds of Formula I, Formula Ia and/or Formula Ib, when being used for in vitro purposes, may be packaged for use as a crystalline solid, an amorphous solid or a lyophilized powder. Suitable quantities range from about 0.1 mg to 1 g. Ideally, the compound is packaged in a container to which a suitable solvent can be added to achieve the desired concentration of solution. Alternatively, the compound may be packaged as an aqueous solution at a fixed concentration, or as a solution in a water-soluble organic solvent at a fixed concentration. Suitable organic solvents may include DMSO, methanol, ethanol or acetonitrile, or mixtures of these solvents with water. Suitable concentrations are about 0.1 mM to about 25 mM.

The present invention includes kits encompassing the compounds of Formula I, Formula Ia and/or Formula Ib, and instructions on how to use said compounds. According to an embodiment, the kit may also include material to differentiate the target cells, and/or a selection of antigens and/or appropriate cell media. The kit will allow a patient's cells to be conveniently activated, isolated and reinjected in a clinical setting. This treatment can be optimized to work best with current clinical therapeutic standards.

The APCs activated with a compound of Formula I, Formula Ia and/or Formula Ib may be administered to a patient in need of immunotherapy in one or more injections. The frequency of injection and the intervals between injections will be adjusted to maximize the therapeutic response. For example, injections may occur once, twice, or more times daily, once, twice, or more times weekly, biweekly, monthly or bimonthly or at any other intervals deemed most suitable to the therapeutic benefit of the patient.

Combination Therapy

A patient in need of immunotherapy may be treated with APCs activated with a compound of Formula I, Formula Ia and/or Formula Ib contemporaneously with other treatments known to the medical practitioner. The use of such multiple treatments may be particularly advantageous to the patient. Such treatments may include, but are not limited to, surgical resection, radiation, chemotherapy, targeted therapy and other types of immunotherapy. Chemotherapy agents that may be used include:

a) cytotoxic agents such as taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof;

b) antimetabolites such as methotrexate, 6-mercaptupurine, 6-thioguanine, cytarabine, 5-fluorouracil decarbazine;

c) alkylating agents such as mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin;

d) anthracyclines such as daunorubicin and doxorubicin;

e) antibiotics such as dactinomycin, bleomycin, mithramycin, and anthramycin (AMC);

f) anti-mitotic agents such as vincristine and vinblastine;

g) targeted therapies that may be used include, but they are not limited to: hormone therapies (such as degarelix an luteinizing hormone-releasing hormone (LHRH) antagonist that reduces testosterone levels in prostate cancer), signal transduction inhibitors (such as imatinib and trastuzumab), as well as gene expression modulators (for example the HDAC inhibitors panobinostat and belinostat), apoptosis inducers (such as recombinant human TNF-related apoptosis-inducing ligand (TRAIL)) and angiogenesis inhibitors (such as sorafenib, sunitinib, pazopanib and everolimus);

h) Immunotherapy agents that may be used include: monoclonal antibodies treatment (anti-CTLA4, anti-PD1), and chimeric receptors (CARs) —T-Cells.

Assays for Measuring Biological Activity

Activity of the compounds of this application may be evaluated using the following assays for TC-PTP-inhibiting activity. Compounds of Formula I will have activities of <10 µM in this assay, and preferably, activity of <1 µM.

1) Enzyme Assay for TC-PTP

Assay buffer: 50 mM Bis-Tris (pH=6.3)
  2 mM EDTA
  5 mM N,N'-dimethyl-N,N'-bis(mercaptoacetyl)hydrazine (DMH)
Substrate: 10 mM fluorescein diphosphate (FDP) store at −20° C. (also can use 10 mM DiFMUP)
Enzyme dilution buffer: 50 mM Bis-Tris (pH=6.3)
  2 mM EDTA
  5 mM DMH
  20% (v/v) glycerol
  0.01% Triton X-100

The assay was carried out at room temperature in 96 well plates. The reaction mixture in 170 µl contained 50 mM Bis-Tris (pH=6.3), 2 mM EDTA, 5 mM N,N'-dimethyl-N,N'bis(mercaptoacetyl)hydrazine (DMH) and 10 µM fluorescein diphosphare (FDP) or 6,8-difluoro-4-methylumbelliferyl phosphate (DiFMUP), 10 µl of 10 concentrations (serial dilution) of the test compound (inhibitor) dissolved in DMSO or DMSO alone for control was added to each well and the plate was mixed for 2 min. The reaction was initiated by adding 20 µl of diluted TC-PTP (50 nM for FDP, 0.5 nM for DiFMUP in 50 mM Bis/Tris (pH=6.3), 2 mM EDTA, 5 mM DMH, 20% glycerol and 0.01% Triton X-100. The phosphatase activity was followed by monitoring the appearance of the fluorescent product fluorescein monophosphate (FMP) or 6,8-difluoro-7-hydroxyl-4-coumarin (DiFMU) continuously for 15-30 min, using the Spectromax Gemini fluorescent plate reader (Molecular probes) with excitation of 440 nm and emission at 530 nm (cutoff filter at 525 nm) for FDP and excitation at 360 nm and emission at 450 nm (cutoff filter at 435 nm) for DIFMUP. All the assays were done at least in duplicate. The initial rate of FMP or DiFMU formation is plotted against the concentration of inhibitor and the data was fitted to 4-parameter equation and the inflection point of the fit is the $IC_{50}$.

2) Mouse Dendritic Cell Assay

Mouse bone marrow cells were flushed from the femur and tibia into RPMI (supplemented with 10% FBS, gentamicin, HEPES, non-essential amino acids) using a syringe equipped with a 23 gauge needle. Clumps were dispersed by gently passing the cell suspension several times through the syringe. Any remaining clumps of cells and debris were removed by passing cell suspension through a 70 µM nylon strainer. The suspension was centrifuged (300×g for 10 mins), the supernatant was discarded and the cells were resuspended in 5 ml of red cell lysis buffer (SIGMA). The cells were counted and mouse monocytes cells (CD11b+) were isolated according to the instructions for positive selection of CD11b cells (Stemcell technologies). The cells were then resuspended in RPMI media supplemented with 10% FBS, gentamicin, Hepes and non-essential aminoacids (aa) and treated with 40 ng/ml of recombinant mouse GM-CSF and IL-4 (Peprotech). Mouse monocytes were plated at $1 \times 10^6$ cells/mL. The cells were incubated for 6 days at 37° C., 5% $CO_2$ in a humidified incubator in the presence of different concentrations of the compounds (0-32 µM). The media was changed every three days by removing half of the media from the plate and replenishing with the same volume of fresh media supplemented with cytokines and the test compounds at the same concentrations.

Immature monocyte-derived DCs may be incubated with a DC maturation cocktail containing the test compounds and incubated for an additional 24-72 hours. There are many DC maturation cocktails identified in the literature, with the "gold standard" consisting of 10 ng/ml TNF-α, 10 ng/ml IL-1β, 1000 units/ml IL-6 and 1 μg/mL PGE2. Alternatively, MPLA (10 μg/mL) and IFNγ (500 U/ml, Peprotech, for clinical research) has also been used. For the data shown in Example 12, the immature monocyte-derived DCs were cultured with LPS (1 μg/mL)) for 48 hours to induce maturation. Test compounds were included in the maturation cocktail at concentrations varying between 1 and 32 μM.

Characteristics of the mature DCs can be determined by a number of assays including flow cytometry analysis of the surface markers expressed on DCs, the cytokine production profile of activated DCs, antigen presentation assay and in vivo experiments to assess the DC-mediated antitumor response and cancer immunity.

3) Human Dendritic Cell Assay

A sample of human blood was diluted with an equal volume PBS plus 2% PBS. The diluted blood was layered on top of Lymphoprep (Stemcell technologies) being careful to minimize the mixing of the blood with Lymphoprep. The mixture was centrifuged at 800×g for 20 minutes at room temperature with brake off. If the blood had been stored for more than 2 hours, the centrifugation time was increased to 30 minutes. The upper plasma layer was then removed and discarded without disturbing the plasma-lymphoprep interface. The mononuclear cell layer (PMBC) at the plasma-lymphoprep interface was removed and retained without disturbing the erythrocyte/granulocyte pellet. The mononuclear cells were washed once with media and the CD14+ cells were isolated according to the instructions for the positive selection of CD14+ kit (Stemcell technologies). The resulting CD14+ cells were cultured in PromoCell monocyte attachment media (PromoCell). Cells were plated at $0.5 \times 10^6$ cells/cm$^2$ and incubated for 1 h at 5% $CO_2$ and 37° C. in a humidified incubator. The PromoCell monocyte attachment media was then replaced with StemXVivo serum-free dendritic cell base media supplemented with gentamicin, 50 ng/mL of recombinant GM-CSF and 35 ng/ml of recombinant IL-4 in the presence of different concentrations of the test compounds (0-32 μM).

The cells were incubated for 6 days at 37° C., 5% $CO_2$ in a humidified incubator. The media was changed every three days by removing half of the media from the plate and replenishing with the same volume of fresh media supplemented with cytokines and test compounds. Alternatively, the entire media volume may be removed and immediately replaced with fresh media containing cytokines and test compounds.

The resulting immature monocyte-derived DCs were treated with MPLA (2.5 μg/mL) and IFNγ (1000 U/ml, Peprotech, for clinical research) and a suitable concentration of the TC-PTP inhibitor and the cells were incubated for an additional 48 hours. Other DC maturation cocktails may also be used including 10 ng/ml TNF-α, 10 ng/ml IL-1β, 1000 units/ml IL-6 and 1 μg/mL PGE2 along with an appropriate concentration of the TC-PTP inhibitor.

Characteristics of the mature DCs can be determined by a number of assays including flow cytometry analysis of the surface markers expressed on DCs, the cytokine production profile of activated DCs, antigen presentation assay and in vivo experiments to assess the DC-mediated antitumor response and cancer immunity.

4) Mouse Syngeneic Tumor Model

A novel dual reporter (GFP & luciferase) MSCV based plasmid was creating by subcloning from two commercially available constructs (addgene 19360: pLenti pgk and addgene 18751: MSCV-IRES-GFP). This construct was used to generate retrovirus for infection of EG7 lymphoma cells (ATCC#CRL-2133). EG 7-ova expressing cells are a commonly used model for T cell lymphoma engineered to express the ovalbumin antigen making them useful in immunological and drug discovery applications. These cells were then GFP sorted at the McGill University life Sciences Complex flow cytometry core (BD FACscalibur) prior to subcutaneous implantation ($5 \times 10^5$ cells) in syngeneic C57bl6 mice (Harlan). Tumors were allowed to establish in the mice and then were imaged ten days post implantation (Perkin Elmer IVIS100) and luminescence was quantified using IVIS software. Mice were then treated on day 10 post injection with $2 \times 10^6$ ex vivo-derived and inhibitor-treated mature dendritic cells (IP injection) (see ex vivo activation of monocyte derived DC with PTP inhibitor). Ovalbulim was added to DC cultures during maturation at a concentration of 2.5 mg/mL. Following maturation, DCs were harvested by gently resuspending with phosphate-buffered saline to dislodge any loosely attached cells. Cells were then spun down and washed twice with phosphate-buffered saline. Prior to injection, DCs were resuspended in phosphate buffered saline at a concentration of 20 million cells per mL.

Preparation of Compounds of the Invention

Synthetic methods for preparing the compounds of the present invention are illustrated in the following Schemes, Methods, and Examples. Starting materials are commercially available or may be prepared according to procedures known in the art or as illustrated herein. In some cases the order of carrying out the foregoing reaction schemes may be varied to facilitate the reaction or to avoid unwanted reaction products. The compounds of the invention are illustrated by means of the specific examples shown below. However, these specific examples are not to be construed as forming the only genus that is considered as the invention. These examples further illustrate details for the preparation of the compounds of the present invention. Those skilled in the art will readily understand that known variations of the conditions and processes of the following preparative procedures can be used to prepare these compounds. All temperatures are in degrees Celsius unless otherwise noted. Mass spectra (MS) were measured by electrospray ion-mass spectroscopy (ESI). $^1$H NMR spectra were recorded on Bruker instruments at 400 or 500 MHz.

List of Abbreviations:
Alk=alkyl
Ar=aryl
BINAP=2,2'-bis(diphenylphosphino)-1,1'-binaphthalene
Boc=tert-butoxycarbonyl
br=broad
$CH_2Cl_2$=dichloromethane
d=doublet
DBU=1,8-diazabicyclo[5.4.0]undec-7-ene
DEAD=diethyl azodicarboxylate
DIBAL=diisobutylaluminum hydride
DIPEA=N,N-diisopropylethylamine
DMF=dimethylformamide
DMSO=dimethyl sulfoxide
ESI=electrospray ionization
EtOAc=ethyl acetate
h=hours
HATU=O-(7-azabenzotriazol-1-yl)-N,N,N',N'-tetramethyl-uronium hexafluorophosphate
HOAc=acetic acid
Hunig's base=diisopropylethylamine
LiOH=lithium hydroxide m=multiplet
MeCN=acetonitrile
MeOH=methyl alcohol
MeTHF=2-methyltetrahydrofuran
$MgSO_4$=magnesium sulfate
min=minutes
MS=mass spectroscopy
MTBE=methyl tert-butyl ether
NaOH=sodium hydroxide
$Na_2SO_4$=sodium sulfate atoms can be non-selectively metalated and trapped with iodine. The resulting, aryl iodide is coupled with the zincate of commercially available diethyl bromodifluoromethylphosphonate. At this point, the $R^1$ group may be refunctionalized to provide phosphonate ester precursors of the current invention. Subsequent ethyl ester hydrolysis and salt formation with a suitable base such as ammonium hydroxide or sodium hydroxide provides the compounds of the current invention. The mixture of products may be separated by chromatography at either of the final two steps.

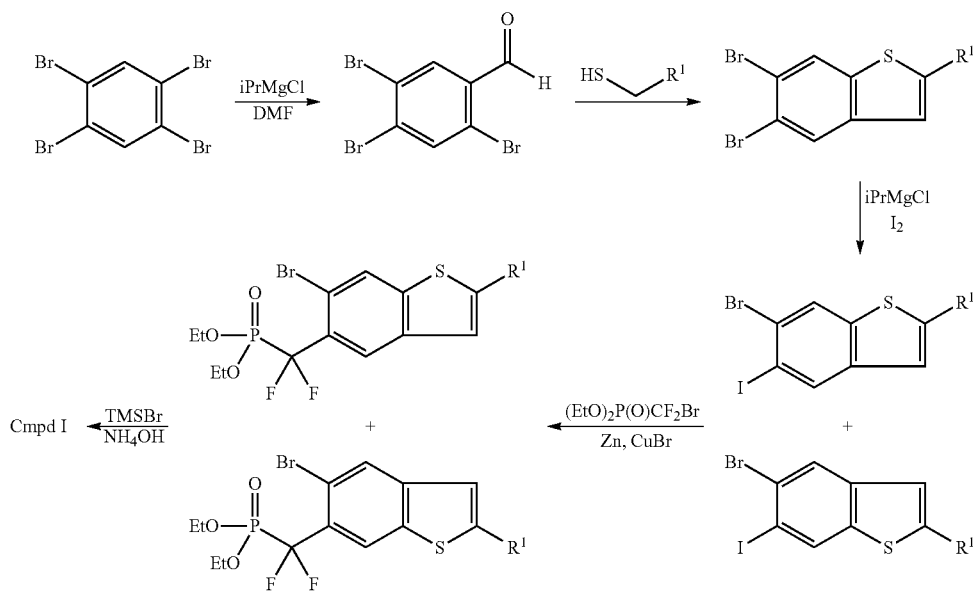

NMP=N-methyl 2-pyrrolidinone
NMR=nuclear magnetic resonance spectroscopy
PG=protecting group
Ph=phenyl
rt=room temperature
s=singlet
t=triplet
TFA=trifluoroacetic acid
TFAA=trifluoroacetic anhydride
THF=tetrahydrofuran
TMEDA=N,N,N',N'-tetramethylethylenediamine Method A:

Compounds of the present invention may be prepared by monometallating tetrabromobenzene followed by trapping with a formylating agent such as DMF. The resulting alpha-halo benzaldehyde can be treated with a suitably-functionalized thiol under basic conditions to displace the bromine adjacent to the aldehyde. If $R^1$ is an electron-withdrawing group, subsequent heating will give aldol condensation with the aldehyde providing formation of the appropriately substituted benzothiophene. One of the remaining bromine Method B:

The methyl ester of commercially available 2-chloro-4-aminobenzoic acid can be selectively iodinated in the 5-position using $I_2$, ICl or other iodinating agents. Reduction of the ester to the corresponding aldehyde followed by treatment with a suitably-functionalized thiol under basic conditions will displace the chlorine adjacent to the aldehyde. If $R^1$ is an electron-withdrawing group, subsequent heating will give aldol condensation with the aldehyde providing formation of the appropriately substituted benzothiophene. A Sandmeyer reaction may be used to convert the aniline nitrogen into a bromine atom. The resulting aryl iodide is coupled with the zincate of commercially available diethyl bromodifluoromethylphosphonate. At this point, the $R^1$ group may be refunctionalized to provide phosphonate ester precursors of the current invention. Subsequent phosphonate ester hydrolysis using TMSBr and salt formation with a suitable base such as ammonium hydroxide or sodium hydroxide provides the compounds of the current invention.

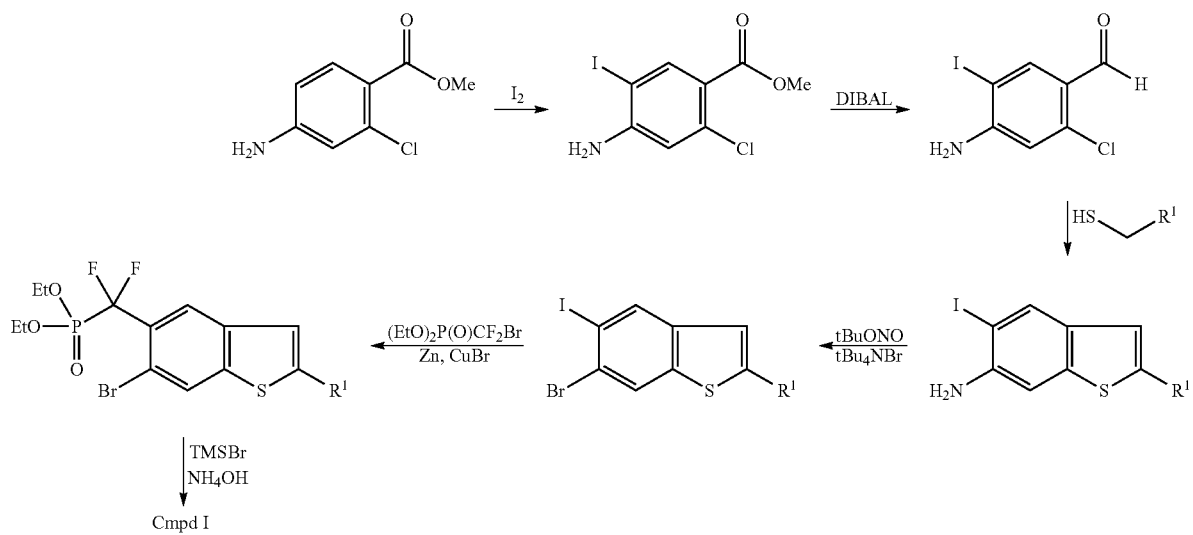

Method C:

The methyl ester of commercially available 2-chloro-4-aminobenzoic acid can be selectively brominated in the 5-position with a reagent such as NBS. Reduction of the ester to the corresponding aldehyde followed by treatment with a suitably-functionalized thiol under basic conditions will displace the chlorine adjacent to the aldehyde. If $R^1$ is an electron-withdrawing group, subsequent heating will give aldol condensation with the aldehyde providing formation of the appropriately substituted benzothiophene. A Sandmeyer reaction may be used to convert the aniline nitrogen into an iodine atom. The resulting aryl iodide is coupled with the zincate of commercially available diethyl bromodifluoromethylphosphonate. At this point, the $R^1$ group may be refuntionalized to provide phosphonate ester precursors of the current invention. Subsequent phosphonate ester hydrolysis using TMSBr and salt formation with a suitable base such as ammonium hydroxide or sodium hydroxide provides the compounds of the current invention.

Method D:

Commercially available 2-fluoro-4-aminobenzoic acid can be selectively brominated in the 5-position using NBS or other brominating agents. A Sandmeyer reaction may be used to convert the aniline nitrogen into an iodine atom, and the acid may be esterified under Fischer conditions. The resulting aryl iodide is coupled with the zincate of commercially available diethyl bromodifluoromethylphosphonate. The ester may be reduced to the alcohol using sodium borohydride or other reducing agents, then oxidized to the aldehyde using an oxidant such as $MnO_2$, Swern or TPAP. Alternatively, this ester may be reduced directly to the aldehyde using DiBAL-H. The alpha-halo aldehyde may be treated with a suitably-functionalized thiol under basic conditions to displace the fluorine adjacent to the aldehyde. If $R^1$ is an electron-withdrawing group, subsequent heating will give aldol condensation with the aldehyde providing formation of the appropriately substituted benzothiophene. At this point, the $R^1$ group may be refuntionalized to provide

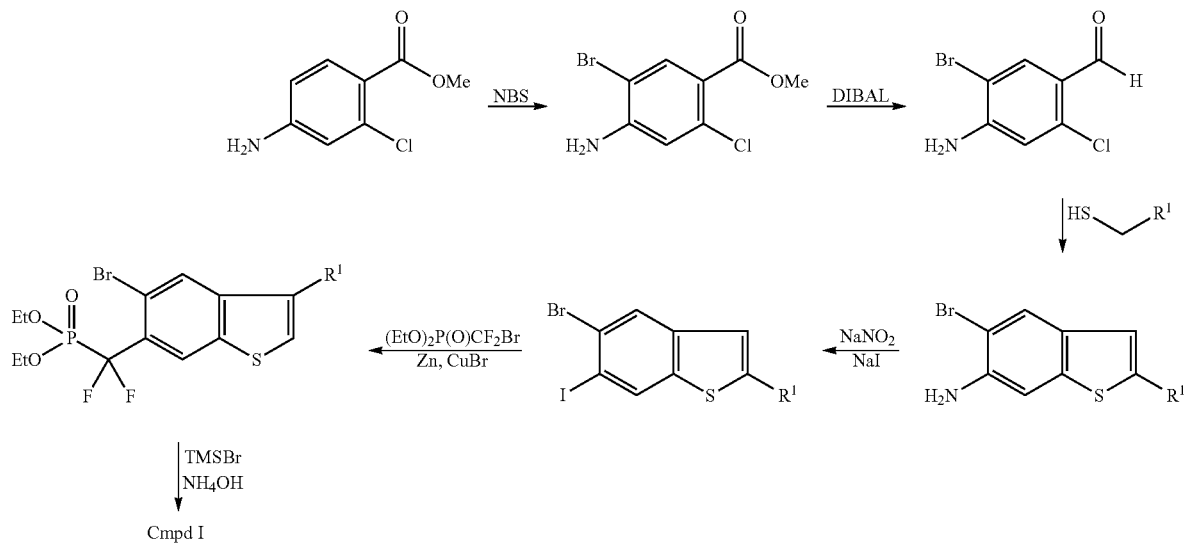

phosphonate ester precursors of the current invention. Subsequent phosphonate ester hydrolysis using TMSBr and salt formation with a suitable base such as ammonium hydroxide or sodium hydroxide provides the compounds of the current invention.

pound as a yellow solid which was used as such in next step without purification. $^1$H NMR (400 MHz, CDCl$_3$); δ 7.78 (d, J=8.6 Hz, 1H), 6.70 (d, J=2.3 Hz, 1H), 6.52 (dd, J=8.6, 2.3 Hz, 1H), 4.09 (bs, 1H), 3.86 (s, 3H). LCMS (M+1)=186.1, 188.1.

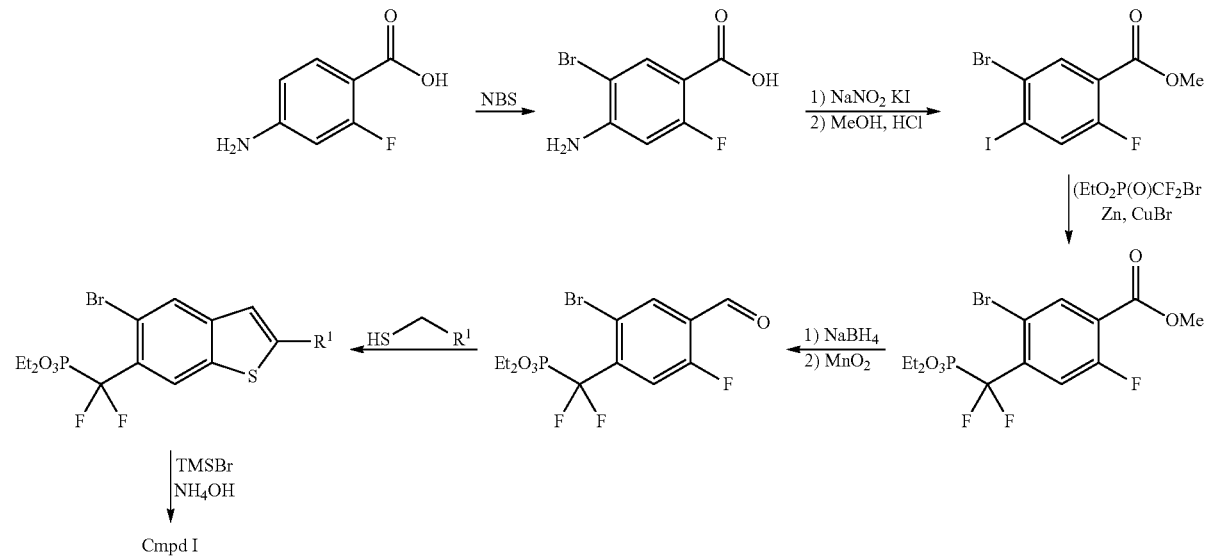

The following Examples are provided to illustrate the invention and are not to be construed as limiting the invention in any manner. The scope of the invention is defined by the appended claims.

EXAMPLE 1

((6-Bromo-2-(Ethoxycarbonyl)Benzo[B]Thiophen-5-Yl)Difluoromethyl)Phosphonate

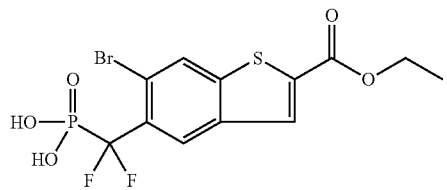 [SMILES: CCOC(=O)c1cc2cc(C(F)(F)P(=O)(O)O)c(Br)cc2s1]

Step 1: methyl 4-amino-2-chlorobenzoate

To methanol at 0° C. was added dropwise acetyl chloride (314.7 mmol, 22.4 mL). After the addition of acetyl chloride, the reaction mixture was stirred at rt for 30 min, then 4-amino-2-chlorobenzoic acid 1 (116.6 mmol, 20.0 g) was added in one portion. The reaction mixture was heated at reflux for 18 hours, cooled to 0° C., and concentrated under vacuum. The residue was suspended in 250 mL of ethyl acetate, cooled to 0° C., and saturated aqueous NaHCO$_3$ was added (pH was 8). The mixture was partitioned and extracted with ethyl acetate (200 mL). Combined organic layers were washed with brine, dried over MgSO$_4$, and concentrated under vacuum to afford 20.9 g of title com- Step 2: methyl 4-amino-2-chloro-5-iodo-benzoate To a suspension of methyl 4-amino-2 chlorobenzoate (20.0 g, 107.75 mmol) and CaCO$_3$ (21.58 g, 215.5 mmol) in MeOH (216 mL) was added a solution of iodine monochloride (20.0 g, 123.2 mmol) in CH$_2$Cl$_2$ (102 mL). The resulting reaction mixture was stirred at room temperature for 5 h, and quenched by adding cooled water 700 mL) and ethyl acetate (700 mL). It was filtered through celite, the filtrate was treated with 300 mL of 10% sodium thiosulfate, partitioned, and the aqueous layer was extracted with ethyl acetate (400 mL). The combined organic layers were washed with 10% sodium thiosulfate (2×), and brine. The organic layer was dried over MgSO$_4$, and concentrated to dryness under vacuum. The residue was adsorbed in silica gel, loaded into flash column which was eluted with 5, 7.5, and 10% ethyl acetate/toluene to afford 17.0 g of title compound as a yellow solid. $^1$H NMR (400 MHz, CDCl$_3$): δ 8.26 (s, 1H), 6.75 (s, 1H), 4.52 (bs, 1H), 3.87 (s, 3H). LCMS (M+1)=312.0, 314.0.

Step 3: (4-amino-2-chloro-5-iodophenyl)methanol

To a solution of methyl 4-amino-2-chloro-5-iodo-benzoate (17.0 g, 54.6 mmol) in CH$_2$Cl$_2$ (400 mL) and THF (100 mL) at −40° C. under nitrogen was slowly added diisobutylaluminum hydride (136.0 mL, 136.0 mmol, 1.0 M in CH$_2$Cl$_2$) over a time period of 30 min. The cooling bath was removed on completion of the addition. After stirring at rt for 2 h, the mixture was poured into a 0° C. saturated aqueous potassium sodium tartrate. The layers were partitioned and the aqueous layer was extracted with CH$_2$Cl$_2$ (600 mL). The combined organic layers were washed with brine, dried over MgSO$_4$, and concentrated to dryness under vacuum to afford 15.5 g of title compound as an orange solid which was used in next step without further purification.

Step 4: 4-amino-2-chloro-5-iodobenzaldehyde

To a solution of (4-amino-2-chloro-5-iodophenyl)methanol (15.5 g, 54.7 mmol) in DMF (270 mL) at rt was added portionwise activated $MnO_2$ (23.8 g, 273.4 mmol). The reaction mixture was stirred at for 18 h. TLC showed incomplete reaction. Additional 15.0 g of MnO2 was added, and the reaction mixture was stirred at rt for additional 18 h, then filtered through celite. The filtrate was diluted with ethyl acetate (400 mL) and water (300 mL). The layers were partitioned and the aqueous layer was extracted with ethyl acetate (300 mL×2). The combined organic layers were washed with brine, dried over $MgSO_4$, and concentrated to dryness under vacuum. The residue was triturated in 50% $Et_2O$/Hexanes to afford 10.2 g of title compound as a yellow solid. $^1H$ NMR (400 MHz, $CDCl_3$) δ 10.12 (d, J=0.8 Hz, 1H), 8.22 (s, 1H), 6.70 (d, J=0.8 Hz, 1H), 4.79 (bs, 1H). LCMS (M+1) 282.0, 283.9.

Step 5: ethyl 6-amino-5-iodobenzo[b]thiophene-2-carboxylate

A suspended solution of 4-amino-2-chloro-5-iodobenzaldehyde (10.2 g, 36.2 mmol) and $K_2CO_3$(12.5 g, 90.6 mmol) in 36 mL of anhydrous DMF was degassed with nitrogen for 15 min, ethyl thioglycolate (8.34 mL 76.1 mmol) was slowly added, then the resulting reaction mixture was stirred at rt for 3 days. Analysis of an aliquot showed about 5% of starting material and 95% of ethyl 2-((5-amino-2-formyl-4-iodophenyl)thio)acetate. The reaction mixture was then heated at 75° C. for 5 h. It was cooled to rt, poured into a mixture of water (500 mL) and $CH_2Cl_2$ (400 mL), and partitioned. The aqueous layer was extracted with $CH_2Cl_2$ (300 mL). The combined organic layers were washed with brine, dried over $MgSO_4$, and concentrated to dryness under vacuum. The residue was triturated in 50% $Et_2O$/Hexanes to afford 5.0 g of title compound as a yellow solid. $^1H$ NMR (400 MHz, $CDCl_3$); δ 8.17 (s, 1H), 7.81 (s, 1H), 7.15 (s, 1H), 4.37 (q, J=7.0 Hz, 2H), 4.30 (s, 2H), 1.40 (t, J=7.0 Hz, 3H). LCMS (M+1)=348.0.

Step 6: ethyl 6-bromo-5-iodobenzo[b]thiophene-2-carboxylate

To a suspended solution ethyl 6-amino-5-iodobenzo[b]thiophene-2-carboxylate 6 (2.4 g, 6.9 mmol) and CuBr (1.0 g, 7.6 mmol) in 69 ml, of anhydrous acetonitrile was added t-butyl nitrite (1.0 mL, 10.34 mmol). The resulting reaction mixture was heated at 45° C. for 6 h, cooled to rt, and poured into 5% sodium thiosulfate. It was extracted with DCM (150 mL×2), the combined organic layers were washed with brine, dried over MgSO4, and concentrated to dryness under vacuum. The residue was adsorbed in silica gel, loaded into flash column which was eluted with 20 and 30% $CH_2Cl_2$/Hexanes to afford 900 mg of title compound as a light yellow solid, $^1H$ NMR (400 MHz, $CDCl_3$) δ 8.38 (s, 1H), 8.15 (s, 1H), 7.15 (s, 1H), 4.44-4.38 (m, 2H), 1.42 (t, J=7.0 Hz, 3H). LCMS (M+1)=410.9, 412.9.

Preparation of Activated Zinc Powder

Zinc powder, in a fritted funnel, was washed with 1.0 N HCl (40 mL×3), $H_2O$ (100 m×5), MeOH (100 mL×3), and $Et_2O$ (100 mL×3). The collected zinc was then placed under high vacuum overnight.

Step 7: ((diethoxyphosphoryl)difluoromethyl)zinc(II)bromide

To a suspended solution of activated Zn powder (2.26 g, 34.56 mmol) in 86 ml of anhydrous THF was added 1,2-dibromoethane (149.0 μL, 1.73 mmol) and the reaction mixture was heated at 50° C. for 15 min. After cooling to rt, trimethylsilyl chloride (262.0 μL, 2.0 mmol) was added, and the mixture was sonicated for 15 minutes. Diethyl (bromodifluoromethyl)phosphonate (6.15 mL, 34.56 mmol) was added dropwise, then the mixture was heated at 50° C. for 1 h. The mix (~0.4 M) was cooled to rt and used directly in the next step.

Step 8: ethyl 6-bromo-5-((diethoxyphosphoryl)difluoromethyl)benzo[b]thiophene-2-carboxylate To a freshly prepared solution of 0.4 M ((diethoxyphosphoryl)difluoromethyl)zinc(II)bromide (14.6 mL, 5.84 mmol) in THF at rt was added CuBr (420 mg, 2.93 mmol) in one portion. The resulting reaction mixture was stirred at rt for 30 min, then a solution of ethyl 6-bromo-5-iodobenzo[b]thiophene-2-carboxylate (from Step 6, 800 mg, 1.95 mmol) in 14.6 mL of anhydrous THF was slowly added. The mixture was heated at 45° C. overnight, cooled to rt, then ethyl acetate (100 mL) and aqueous saturated ammonium chloride (100 mL) were added. The mixture was partitioned and the aqueous layer was extracted with ethyl acetate (100 mL). The combined organic layers were washed with brine, dried over $MgSO_4$, and concentrated to dryness under vacuum.

The residue was adsorbed on silica gel, then loaded onto flash column which was eluted with 5, 7, 10, and 12% ethyl acetate/toluene to afford 260 mg of title compound as yellow solid. 300 mg of starting material was recovered. $^1H$ NMR (400 MHz, $CDCl_3$); δ 8.19 (s, 1H), 8.16 (s, 1H), 8.04 (s, 1H), 4.44-4.40 (m, 2H), 4.32-4.21 (m, 4H), 1.42 (t, J=7.2 Hz, 3H), 1.39-1.32 (m, 6H). LCMS (M+1)=471.0, 473.0.

Step 9: bis-ammonium ((6-bromo-2-(ethoxycarbonyl)benzo[b]thiophen-5-yl)difluoromethyl)phosphonate To a stirred solution of ethyl 6-bromo-5-((diethoxyphosphoryl)difluoromethyl)benzo[b]thiophene-2-carboxylate (40 mg, 0.09 mmol) in 1 mL of anhydrous dichloromethane at rt was added trimethylsilyl bromide (112 μL, 0.85 mmol). The reaction mixture was stirred at rt overnight, concentrated to dryness under vacuum co-evaporated with dichloromethane (3×), and ethanol (3×). The residue was dissolved in 0.5 mL of ethanol, and 1.0 mL of ammonia (0.5 M in dioxane) was added. The suspension was stirred for 30 min, concentrated to dryness under vacuum, and the residue was triturated in $Et_2O$ to afford 20 mg of the title compound as a colorless powder. $^1H$ NMR (400 MHz, MeOH-d4): δ 8.42 (s, 1H), 8.26 (s, 1H), 8.11 (s, 1H), 4.39 (q, J=7.1 Hz, 2H), 1.40 (t, J=7.1 Hz, 3H). LCMS (M+1)=414.9, 416.9.

EXAMPLE 2

6-Bromo-5-(Difluoro(Phosphonato)Methyl)Benzo[B]Thiophene-2-Carboxylate

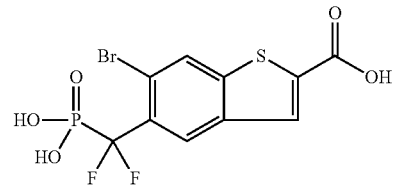 [SMILES: O=C(O)c1cc2cc(C(F)(F)P(=O)(O)O)c(Br)cc2s1]

Step 1: 6-bromo-5-((ethoxy(hydroxy)phosphoryl) difluoromethyl)benzo[b] thiophene-2-carboxylic acid To a stirred solution of ethyl 6-bromo-5-((diethoxyphosphoryl)difluoromethyl)benzo[b]thiophene-2-carboxylate 8 (Example 1, Step 8; 120 mg, 0.25 mmol) in 0.90 mL of ethanol and 1.60 mL THF at 0° C. was added dropwise 1N LiOH (380 μL, 0.38 mmol). The cooling bath was removed, and the reaction mixture was stirred at rt for 3 h. The solution was cooled to 0° C., 1N HCl was added to reach pH 2 and the mixture was extracted with ethyl acetate (2×). The combined organic layers were washed with brine, dried over MgSO$_4$, and concentrated to dryness under vacuum. The residue was purified by flash column eluting with 10% MeOH/CH$_2$Cl$_2$ and i-PrOH/NH$_4$OH/H$_2$O (12:3:1) to afford 51 mg of the title compound as a colorless solid. $^1$H NMR (400 MHz, MeOH-d4): δ 8.31 (s, 1H), 8.26 (s, 1H), 8.09 (s, 1H), 4.18-4.10 (m, 2H), 1.29 (s, J=7.04 Hz, 3H). LCMS (M+1)=415.0, 417.0.

Step 2: tris-ammonium 6-bromo-5-(difluoro(phosphonato)methyl)benzo[b]thiophene-2-carboxylate To a stirred solution of 6-bromo-5-((ethoxy(hydroxy) phosphoryl)difluoromethyl)benzo[b]thiophene-2-carboxylic acid 11 (51 mg, 0.12 mmol) in 1 mL of anhydrous dichloromethane at rt was added trimethylsilyl bromide (162 μL, 1.2 mmol). The reaction mixture was stirred at rt overnight, concentrated to dryness under vacuum, co-evaporated with dichloromethane (3×), and ethanol (3×). The residue was dissolved in 0.5 mL of ethanol, and 1.0 mL of ammonia (0.5M dioxane) was added. It was stirred for 30 min, concentrated to dryness under vacuum, and the residue was triturated in i-PrOH/NH$_4$OH/H$_2$O (12:3:1) afford 26 mg of the title compound as a colorless powder. $^1$H NMR (400 MHz, D$_2$O): δ 8.15 (s, 1H), 8.07 (s, 1H) 7.72 (s, 1H). LCMS (M+1)=386.9, 388.9.

EXAMPLE 3

((6-Bromo-2-Carbamoylbenzo[B]Thiophen-5-Yl) Difluoromethyl)Phosphonate

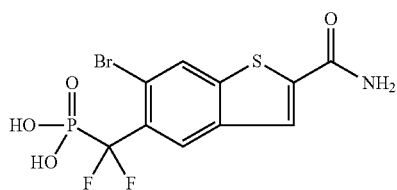 [SMILES: NC(=O)c1cc2cc(C(F)(F)P(=O)(O)O)c(Br)cc2s1]

Step 1: ethyl hydrogen ((6-bromo-2-carbamoylbenzo[b]thiophen-5-yl)difluoromethyl)phosphonate To stirred solution of ethyl 6-bromo-5-((diethoxyphosphoryl)difluoromethyl)benzo[b]thiophene-2-carboxylate (Example 1, Step 8; 60 mg, 0.13 mmol) in 0.50 mL, of THF at rt was added 0.50 mL ammonium hydroxide (28-30%/H$_2$O). The mixture was heated at 65° C. overnight, and concentrated to dryness under vacuum. The residue was purified by flash column eluting with i-PrOH/NH$_4$OH/H$_2$O (54:2.5:0.5 to 30:2.5:0.5). The fractions were concentrated under vacuum, the residue was suspended in ethyl acetate, and 1N HCl was added to adjust pH 2. The mixture was partitioned and the aqueous layer was extracted with ethyl acetate. The combined organic layers were washed with brine, dried over MgSO$_4$, and concentrated to dryness under vacuum to afford 26 mg of title compound as yellow solid. $^1$H NMR (400 MHz, MeOH-d4): δ 8.33 (s, 1H), 8.19 (s, 1H), 8.04 (s, 1H), 4.21-4.14 (m, 2H), 1.33-1.27 (m, 3H), LCMS (M+1)=414.0, 416.0.

Step 2: bis-ammonium ((6-bromo-2-carbamoylbenzo[b]thiophen-5-yl)difluoromethyl)phosphonate To a stirred solution of ethyl hydrogen ((6-bromo-2-carbamoylbenzo[b]thiophen-5-yl)difluoromethyl)phosphonate (26 mg, 0.06 mmol) in 1 mL of anhydrous dichloromethane at rt was added trimethylsilyl bromide (83 μL, 0.63 mmol). The reaction mixture was stirred at rt overnight. LCMS showed incomplete reaction; additional 160 μL of trimethylsilyl bromide was added. It was stirred at rt overnight, concentrated to dryness under vacuum, co-evaporated with dichloromethane (3×), and ethanol (3×). The residue was dissolved in 0.5 of ethanol, and 1.0 mL of ammonia (0.5M in dioxane) was added. It was stirred for 30 min, concentrated to dryness under vacuum, and the residue was triturated in 2-propanol to afford 15 mg of the title compound as a light yellow powder. $^1$H NMR (400 MHz, D$_2$O): δ 8.13 (2s, 2H), 7.83 (s, 1H), LCMS (M+1) 385.8, 387.9.

EXAMPLE 4

((6-Bromo-2-Cyanobenzo[B]Thiophen-5-Yl)Difluoromethyl)Phosphonate

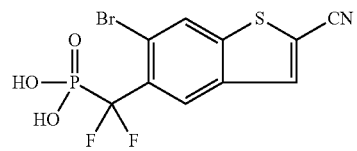 [SMILES: N#Cc1cc2cc(C(F)(F)P(=O)(O)O)c(Br)cc2s1]

Step 1: ethyl methyl ((6-bromo-2-cyanobenzo[b] thiophen-5-yl)difluoromethyl)phosphonate POCl$_3$ (2 was added to ethyl hydrogen ((6-bromo-2-carbamoylbenzo[b]thiophen-5-yl)difluoromethyl)phosphonate (Example 3, Step 1; 26 mg, 0.06 mmol), and the reaction mixture was heated at 90° C. overnight. It was concentrated to dryness under vacuum, and then 2 mL of anhydrous methanol was added, stirred at rt for 30 min. The mixture was then concentrated to dryness under vacuum. The residue was purified by Isco Combiflash eluting with 0 to 60% EtOAc/hexanes to afford 8 mg of the title compound. $^1$H NMR (400 MHz, CDCl$_3$): δ 8.21 (s, 1H), 8.18 (s, 1H), 7.91 (s, 1H), 4.33-4.27 (m, 2H), 3.92 (s, 1.5H), 3.89 (s, 1.51), 1.37 (t, J=7.0 Hz, 3H), LCMS (M+1)=410.0, 412.0.

Step 2: bis-ammonium ((6-bromo-2-cyanobenzo[b] thiophen-5-yl)difluoromethyl)phosphonate To a stirred solution of ethyl methyl ((6-bromo-2-cyanobenzo[b]thiophen-5-yl) difluoromethyl)phosphonate (8 mg, 0.02 mmol) in 1 mL of anhydrous dichloromethane at rt was added trimethylsilyl bromide (52 μL, 0.4 mmol). The reaction mixture was stirred at rt over weekend, concentrated to dryness under vacuum, co-evaporated with dichloromethane (3×), and ethanol (3×). The residue was dissolved in 0.5 mL of ethanol, and 1.0 of ammonia (0.5 M in dioxane) was added. The suspension was stirred for 30 min, concentrated to dryness under vacuum, and the residue was triturated in 2-propanol to afford 3 mg of the title compound, $^1$H NMR (400 MHz, D$_2$O): δ 8.27 (s, 1H), 8.18 (s, 1H), 8.04 (s, 1H), LCMS (M+1)=367.8, 369.9.

EXAMPLE 5

((6-Bromo-2-(Hydroxymethyl)Benzo[B]Thiopen-5-Yl)Difluoromethyl)Phosphonate

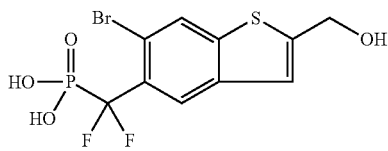

Step 1: diethyl ((6-bromo-2-(hydroxymethyl)benzo[b]thiophen-5-yl)difluoromethyl)phosphonate To a suspension of ethyl 6 bromo-5-((diethoxyphosphoryl)difluoromethyl)benzo[b]thiophene-2-carboxylate (200 mg, 0.42 mmol) and sodium borohydride (96 mg, 2.55 mmol) in 1.0 mL of THF at 65° C. was added dropwise anhydrous methanol (300 μL) over 30 min. The reaction was kept at 65° C. for 3 h, cooled to rt, poured into 1N HCl, extracted with EtOAc (2×). The combined organic layers were washed with brine, dried over MgSO$_4$, and concentrated to dryness under vacuum. The residue was purified by Isco Combiflash (24 g column) eluting with 0 to 90% EtOAc/hexanes to afford 100 mg of the title compound as a yellow solid. $^1$H NMR (400 MHz, CDCl$_3$) δ 8.10 (s, 1H), 7.96 (s, 1H), 7.14 (s, 1H) 4.89 (s, 2H), 4.29-4.18 (m, 4H), 1.36-1.25 (m, 6H), LCMS (M+1)=429.1, 431.1.

Step 2: bis-ammonium ((6-bromo-2-(hydroxymethyl)benzo[b]thiophen-5-yl)difluoromethyl)phosphonate To a stirred solution diethyl ((6-bromo-2-(hydroxymethyl)benzo[b]thiophen-5-yl)difluoromethyl)phosphonate (100 mg, 0.23 mmol) in 2 mL of anhydrous dichloromethane at rt was added trimethylsilyl bromide (307 μL, 2.30 mmol). The reaction mixture was stirred at rt overnight, concentrated to dryness under vacuum, co-evaporated with dichloromethane (3×), and ethanol (3×). The residue was purified by flash chromatography on C-18 eluting with 10-20% EtOH/H$_2$O. Fractions were collected, and concentrated to dryness under vacuum. The residue was dissolved in 0.5 mL of ethanol, and 1.0 mL of ammonia (0.5M in dioxane) was added. It was stirred for 30 min, concentrated to dryness under vacuum, and the residue was triturated in 2-propanol to afford 9 mg of the title compound as a yellow solid, $^1$H NMR (400 MHz, D$_2$O): δ 8.13 (s, 1H), 8.10 (s, 1H), 7.24 (s, 1H), 4.75 (s, 2H). LCMS (M+1)=372.9, 375.9.

EXAMPLE 6

((6-Bromo-2-(Cyanomethyl)Benzo[B]Thiophen-5-Yl)Difluoromethyl)Phosphonate

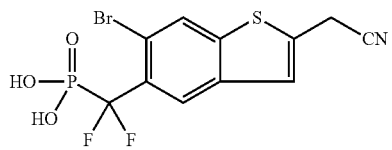 [SMILES: O=P(O)(O)C(F)(F)c1cc2cc(CO)sc2cc1Br]

Step 1: diethyl ((6-bromo-2-(chloromethyl)benzo[b]thiophen-5-yl)difluoromethyl)phosphonate To a stirred solution of diethyl ((6-bromo-2-(hydroxymethyl)benzo[b]thiophen-5-yl)difluoromethyl)phosphonate (Example 5, Step 1; 60 mg, 0.14 mmol) in anhydrous dioxane (1 mL) at 0° C. was added thionyl chloride (16 μL, 0.22 mmol). The reaction mixture was at rt for 3 h, then additional thionyl chloride (16 μL, 0.22 mmol) was added, and stirred for 2 h. It was concentrated to dryness under vacuum. The residue was purified by flesh chromatography eluting with 20 to 40% EtOAc/hexanes to afford 37 mg of the title compound as a colorless gum. $^1$H NMR (400 MHz, CDCl$_3$): δ 8.12 (s, 1H), 8.02 (d, J=1 Hz, 1H), 7.31 (d, J=1 Hz, 1H), 4.84 (s, 2H), 4.38-4.20 (m, 4H), 1.37-1.34 (m, 6H), LCMS (M+1)=447.0, 449.0.

Step 2: diethyl ((6-bromo-2-cyanomethyl)benzo[b]thiophen-5-yl)difluoromethyl)phosphonate To a stirred solution of diethyl ((6-bromo-2-(chloromethyl)benzo[b]thiophen-5-yl)difluoromethyl)phosphonate (36 mg, 0.08 mmol) in DMSO (1 mL) at rt was added potassium cyanide (7 mg, 0.1 mmol). The reaction mixture was at rt for 5 h, then sonicated for 1 h (temperature of water bath reached 45° C.). It was cooled to rt, poured into a mixture of H$_2$O:EtOAc (1:1), partitioned, and the aqueous layer was extracted with EtOAc. The combined organic layers were washed with brine, dried over MgSO$_4$, and concentrated to dryness under vacuum. The residue was purified by flash chromatography eluting with 50 to 60% EtOAc/hexanes to afford 9 mg of the title compound as a yellow solid. $^1$H NMR (400 MHz, CDCl$_3$): δ 8.11 (s, 1H), 8.03 (s, 1H), 7.34 (s, 1H), 4.31-4.21 (m, 4H), 3.99 (s, 2H), 1.38-1.25 (m, 6H). LCMS (M+1)=438.0, 440.0.

Step 3: bis-ammonium ((6-bromo-2(cyanomethyl)benzo[b]thiophen-5-yl)difluoromethyl)phosphonate To a stirred solution of diethyl ((6-bromo-2-(cyanomethyl)benzo[b]thiophen-5-yl)difluoromethyl)phosphonate (9 mg, 0.02 mmol) in 5 mL of anhydrous dichloromethane at rt was added trimethylsilyl bromide (27 μL 0.20 mmol). The reaction mixture was stirred at rt overnight, LCMS showed incomplete reaction. It was sonicated for 3 h (temperature of water bath reached 45° C.), concentrated to dryness under vacuum, co-evaporated with dichloromethane (3×), and ethanol (3×). The residue was dissolved in 0.5 mL of ethanol, and 1.0 mL of ammonia (0.5M in dioxane) was added. The suspension was stirred for 30 min, concentrated to dryness under vacuum, and the residue was triturated in 2-propanol to afford 7 mg of the title compound. ¹H NMR (400 MHz, D₂O): δ 8.11 (s, 1H), 7.33 (s, 1H), 4.10 (s, 2H), LCMS (M+1)=381.9, 383.9.

EXAMPLE 7

((5-Bromo-2-(Ethoxycarbonyl)Benzo[B]Thiophen-6Yl)Difluoromethyl)Phosphonate

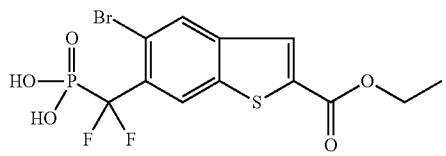 [SMILES: CCOC(=O)c1cc2cc(Br)c(C(F)(F)P(=O)(O)O)cc2s1]

Step 1: methyl 4-amino 5-bromo-2-chlorobenzoate

To a stirred solution of methyl 4-amino-2-chlorobenzoate (10.9 g, 58.73 mmol) in 196 mL of THF at rt was added NBS (11.5 g, 64.6 mmol). The reaction mixture was stirred at rt over weekend, 200 mL of EtOAc were added, and the organic layer was washed with 10% sodium thiosulfate, followed by 10% sodium carbonate, and brine. The organic layer was dried over MgSO₄ and concentrated to dryness under vacuum. The residue was adsorbed on silica gel, loaded onto a flash column and eluted with 10-30% EtOAc/hexanes. Mixed fractions were purified again by flash chromatography eluting with 8% EtOAc/toluene to afford in total 9.58 g of the title compound as a light yellow solid. ¹H NMR (400 MHz, CDCl₃); δ 8.03 (s, 1H), 6.79 (s, 1H), 4.52 (bs, 2H), 3.87 (s, 3H) LCMS (M+1)=263.9, 265.9.

Step 2: (4-amino-6-bromo-2-chlorophenyl)methanol

To a solution of methyl 4-amino-5-bromo-2-chlorobenzoate (16.73 g, 63.25 mmol) in dichloromethane (650 mL) at −40° C. under nitrogen was slowly added diisobutylaluminum hydride (158 mL, 158 mmol, 1.0 M/CH₂Cl₂) over 30 min; the cooling bath removed on completion of addition. After stirring at rt for 2 h, the mixture was poured into a 0° C. saturated aqueous potassium sodium tartrate. The layers were separated and the aqueous layer was extracted with dichloromethane (600 mL). The combined organic layers were washed with brine, dried over MgSO₄, and concentrated to dryness under vacuum. The residue was adsorbed on silica gel, loaded onto a flash column which was eluted with 10-15% ethyl acetate/toluene to afford 10.8 g of title compound as a orange solid. ¹H NMR (400 MHz, CDCl₃): δ 7.49 (s, 1H), 6.78 (s, 1H), 4.64 (s, 2H) 4.15 (bs, 2H), LCMS (M+1)=236.0, 238.0.

Step 3: 4-amino-5-bromo-2-chlorobenzaldehyde

To a solution of (4-amino-5-bromo-2-chlorophenyl)methanol (10.8 g, 45.7 mmol) in DMF (229 mL) at rt was added portionwise activated MnO₂ (19.9 g, 228.3 mmol). The reaction mixture was stirred at for 18 h and filtered through celite. The filtrate was diluted with ethyl acetate (300 mL) and water (200 mL), the layers were partitioned, and the aqueous layer was extracted with ethyl acetate (200 mL). The combined organic layers were washed with brine, dried over MgSO₄, and concentrated to dryness under vacuum to afford 10.7 g of title compound as an orange solid. ¹H NMR (400 MHz, CDCl₃): δ 10.16 (s, 1H), 8.02 (s, 1H) 6.75 (s, H), 4.81 (bs, 2H), LCMS (M+1)=234.0, 236.0.

Step 4: ethyl 6-amino-5-bromobenzo[b]thiophene-2-carboxylate

A suspension of 4-amino-5-bromo-2-chlorobenzaldehyde (10.6 g, 45.2 mmol) and K₂CO₃ (15.6 g, 113.0 mmol) in 45 mL of anhydrous DMF was degassed with nitrogen for 15 min then cooled to 0° C. Ethyl thioglycolate (5.9 mL, 54.25 mmol) was slowly added and the resulting reaction mixture was stirred at rt overnight. LCMS showed about 50% conversion; additional ethyl thioglycolate (5.9 mL, 54.25 mmol) was added and stirred at rt overnight. The mixture was then heated at 75° C. for 5 h, cooled to rt, and poured into a mixture of water (500 mL) and CH₂Cl₂ (400 mL). The layers were separated and the aqueous layer was extracted with CH₂Cl₂ (300 mL). The combined organic layers were washed with brine, dried over MgSO₄, and concentrated to dryness under vacuum. The residue was purified by flash chromatography eluting with 30-50% CH₂Cl₂/hexanes. Fractions were collected and concentrated to dryness under vacuum. The residue was triturated in 50% Et₂O/hexanes (60 mL) to afford 3 g of the title compound as a yellow solid. ¹H NMR (400 MHz, CDCl₃): δ 7.93 (s, 1H) 7.83 (s, 1H), 7.15 (s, 1H), 4.37 (q, J=7.2 Hz, 2H) 4.15 (bs, 2H), 1.39 (t, J=7.2 Hz, 3H). LCMS (M+1)=300.0, 302.0.

Step 5: ethyl 5-bromo-6-iodobenzo[b]thiophene-2-carboxylate

To a suspension of ethyl 6 amino-5-bromobenzo[b]thiophene-2-carboxylate (2.12 g, 7.06 mmol) and CuI (1.48 g, 7.76 mmol) in 15 mL of anhydrous acetonitrile was added t-butyl nitrite (1.26 mL, 10.60 mmol). The resulting reaction mixture was heated at 45° C. for 6 h, cooled to rt, and poured into 5% sodium thiosulfate. It was extracted with CH₂Cl₂ (150 mL×2) and the combined organic layers were washed with brine, dried over MgSO₄, and concentrated to dryness under vacuum. The residue was adsorbed on silica gel, loaded onto flash column and eluted with 20 to 30% CH₂Cl₂/hexanes to afford 400 mg of title compound, ¹H NMR (400 MHz, CDCl₃): δ 8.38 (s, 1H), 8.16 (s, 1H), 7.90 (s, 1H), 4.46-4.39 (m, 2H), 1.42 (t, J=7.0 Hz, 3H), LCMS (M+1) 410.9, 412.9.

Step 6: ethyl 5-bromo-6-((diethoxyphosphoryl)difluoromethyl)benzo[b]thiophene-2-carboxylate To a freshly prepared solution of 0.4 M ((diethoxyphosphoryl)difluoromethyl)zinc(II) bromide (Example 1, Step 7; 7.5 mL 3.0 mmol) in THF at rt was added CuBr (215 mg, 1.5 mmol) in one portion. The resulting mixture was stirred at rt for 30 min, then a solution of ethyl 5-bromo-6-iodobenzo[b]thiophene-2-carboxylate (400 mg, 1.33 mmol) in 7.5 mL of anhydrous THF was slowly added. The mixture was heated at 45° C. overnight, cooled to rt, then ethyl acetate (80 mL) and aqueous saturated ammonium chloride (80 mL) were added. The layers were partitioned and the aqueous layer was extracted with ethyl acetate (80 mL). The combined organic layers were washed with brine, dried over MgSO₄, and concentrated to dryness under vacuum. The residue was adsorbed on silica gel, loaded onto flash column and eluted with 5-10% ethyl acetate/toluene to afford 55 mg of title compound. ¹H NMR (400 MHz, CDCl₃): δ 8.17 (s, 1H), 8.14 (s, 1H), 7.96 (s, 1H), 4.42 (d, J=7.0 Hz, 2H), 4.3-4.20 (m 4H), 1.40 (t, J=7.0 Hz, 3H), 1.37-1.33 (m, 6H), LCMS (M+1)=471.0, 473.0.

Step 7: bis-ammonium ((5-bromo-2-(ethoxycarbonyl)benzo[b]thiophen-6-yl)difluoromethyl)phosphonate To a stirred solution of ethyl 5-bromo-6-((diethoxyphosphoryl)difluoromethyl)benzo[b]thiophene-2-carboxylate (55 mg, 0.12 mmol) in 1 mL of anhydrous dichloromethane at rt was added trimethylsilyl bromide (178 µL, 1.16 mmol). The reaction mixture was stirred at rt overnight, concentrated to dryness under vacuum, co-evaporated with dichloromethane (3×) and ethanol (3×). The residue was dissolved in 0.5 mL of ethanol, and 1.0 mL of ammonia (0.5M in dioxane) was added. It was stirred for 30 min, concentrated to dryness under vacuum, and the residue was triturated in Et₂O to afford 43 mg of the title compound as a colorless powder. ¹H NMR (400 MHz, MeOH-d4): δ 8.55 (s, 1H), 8.22 (s, 1H), 8.03 (s, 1H), 4.40 (q, J=7.1 Hz, 2H), 1.40 (t, J=7.1 Hz, 3H). LCMS (M+1)=415.0, 417.0.

EXAMPLE 8

((5-Bromo-2-(Methoxycarbonyl)Benzo[B]Thiophen-6-Yl)Difluoromethyl)Phosphonate

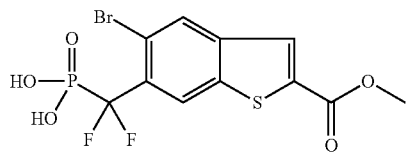 [SMILES: COC(=O)c1cc2cc(Br)c(C(F)(F)P(=O)(O)O)cc2s1]

Step 1: Amino-5-bromo-2-fluorobenzoic acid

To a −10° C. solution of 4-amino-2-fluorobenzoic acid 1 (18 g, 116.0 mmol) in 116 mL of THF was added N-bromosuccinimide (22.3 g, 125.3 mmol) in small portions over a period of 40 min while maintaining the internal temperature below −5° C. The reaction was allowed to warm to room temperature and stirred for 18 h. After removal of THF under vacuum, the residue was dissolved in 58 mL of DMF, 116 mL of water was slowly added to induce precipitation. The mixture was vigorously stirred for 1 h, then filtered, washed with water and dried under vacuum to afford 20.7 g of a yellow solid. Trituration in 120 mL of ethyl acetate provided 14.5 g of title compound as a light yellow solid, 1H NMR (400 MHz, DMSO-d6) δ 12.60 (s, 1H), 7.78 (d, J=7.4 Hz, 1H), 6.50 (d, J=13.3 Hz, 1H), 6.34 (s, 2H), LCMS (M+1): 234.0 and 236.0.

Step 2: 5-Bromo-2-fluoro-4-iodobenzoic acid

To a 0° C. suspension of 4-amino-3-bromo-2-fluorobenzoic acid (15.58 g, 66.58 mmol) in 370 mL of water was added 53.3 mL of concentrated HCl dropwise. A solution of sodium nitrite (5.05 g, 73.33 mmol) in water (49 mL) was added slowly to maintain the internal temperature <10° C. The resulting suspension was warmed to rt and stirred 1 h until it formed a solution. Water (290 mL) was charged in 3-neck flask equipped with a mechanical stirrer, potassium iodide (55.3 g, 332.9 mmol) was added and the resulting solution was warmed to 30° C. The solution of diazonium salt was transferred slowly over 1 h to the potassium iodide solution so as to control the rate of gas evolution and maintain the internal temperature at 35° C. The flask containing the diazonium salt was rinsed with a solution of water (25 mL) and concentrated HCl (2.5 mL) which was then added to the KI solution. The resulting suspension was stirred 30° C. overnight. The solids were filtered and washed twice with water then dried to give 20.3 g of crude 5-bromo-2-fluoro-4-iodobenzoic acid as a yellow solid which was used in next step without further purification.

Step 3: Methyl 5-bromo-2-fluoro-4-iodobenzoate

To methanol (118 mL) at 0° C. was added dropwise acetyl chloride (11.3 mL, 158.9 mmol). After the addition of acetyl chloride complete, the solution was stirred at rt for 30 min, then 5-bromo-2-fluoro-4-iodobenzoic acid (20.3 g, 58.9 mmol) was added in one portion. The reaction mixture was heated at reflux for 4 h, cooled to 0° C., and concentrated under vacuum. The residue was suspended in 50 mL of diethyl ether, warmed up to 40° C., and 30 mL of hexanes was added. The suspension mixture was stirred at rt for 90 m filtered and the solid was washed with 15 mL of hexanes-Et2O (2:1). The collected solid was dried under vacuum to afford 13.52 g of the title compound as a yellow solid. 1H NMR (400 MHz, CDCl3): δ 8.14-8.13 (m, 1H), 7.69-7.66 (m, 1H), 3.93 (s, 3H).

Step 4: Methyl 5-bromo-4-((diethoxyphosphoryl)difluoromethyl)-2-fluorobenzoate

To a suspension of Zn dust (4.93 g, 75.33 mmol) in degassed, anhydrous THF (19.7 mL) was added TMSCl (3.33 mL, 26.37 mmol) and the suspension heated to 50° C. for 1.5 h with vigorous stirring. The contents are cooled to 30° C. and a solution of diethyl (bromodifluoromethyl)phosphonate (20.1 g, 75.33 mmol) in THF (81 mL) was added dropwise (temperature kept between 40-45° C.). The reaction mixture was stirred at 30° C. for 2 h (the clouded suspension became solution with some deposit). Copper bromide (10.81 g, 75.33 mmol) was flame dried and suspended in anhydrous DMAC (21.5 mL). The organozinc solution was slowly transferred to the suspended copper bromide, and the mixture was stirred at rt for 30 min. A solution of methyl 5-bromo-2-fluoro-4-iodobenzoate 4 (13.52 g, 37.67 mmol) in DMAC (54 mL) was slowly added to the reaction mixture, it was heated to 50° C. for 8 h. The reaction mixture was cooled to rt and poured into a mixture of water-ethyl acetate (1:1). The layers were separated and the aqueous layer was extracted with ethyl acetate (2×). The combined organic layers were sequentially washed with water, 3% ammonium hydroxide and brine, then dried over MgSO4 and evaporated to dryness to provide 19 g of crude material which was put under high vacuum for 36 h. The crude material was purified by column chromatography eluting with 10-40% ethyl acetate/hexanes to afford 12.2 g of the title compound as a light yellow oil. 1H NMR (400 MHz, DMSO-d6) δ 8.15 (d, J=6.7 Hz, 1H), 7.60-7.57 (m, 1H), 4.20-4.16 (m, 4H), 3.87 (s, 3H), 1.24 (t, J=7.0 Hz, 6H).

Step 5: Diethyl((2-bromo-5-fluoro-4-(hydroxymethyl)phenyl)difluoromethyl)phosphate To a suspension of methyl 5-bromo-4-((diethoxyphosphoryl)difluoromethyl)-2-fluorobenzoate (12 g, 28.63 mmol) and sodium borohydride (5.4 g, 143.15 mmol) in THF (140 mL) at 65° C. was added methanol (10 mL) so as to control gas evolution. After addition of methanol (30 minutes), the reaction mixture was cooled to 0° C. and aqueous saturated ammonium chloride was slowly added. The mixture was extracted with dichloromethane (2×), the combined organic layers were washed with brine, dried over MgSO4 and evaporated to dryness. The crude material was purified by column chromatography eluting with 30% and 65% ethyl acetate/hexanes to afford 7 g of the title compound as a colorless solid. 1H NMR (400 MHz, DMSO-d6) δ 7.79 (δ, J=7.0 Hz, 1H), 7.37-7.34 (m, 1H), 5.53 (t, J=5.9 Hz, 1H), 4.57 (d, J=5.9 Hz, 2H), 4.21-4.11 (m, 4H), 1.24 (t, J=7.0 Hz, 6H).

Step 6: Diethyl ((2-bromo-5-fluoro-4-formylphenyl) difluoromethyl)phosphonate

To a solution of diethyl ((2-bromo-5-fluoro-4-(hydroxymethyl)phenyl)difluoromethyl)phosphonate (7.0 g, 17.9 mmol) in anhydrous DMF (71 m) at rt was added activated MnO2 (15.6 g, 179.0 mmol). The reaction mixture was stirred at rt for 18 h, then heated to 60° C. for 4h, Diethyl ether (71 mL) and water (71 mL) were added to the reaction mixture and it was filtered through celite. The layers were separated and the aqueous layer was extracted with diethyl ether (2×) The combined organic layers were sequentially washed with water and brine, dried over MgSO4 and evaporated to dryness. The crude material was purified by column chromatography eluting with 20-65% ethyl acetate/hexanes to afford 2.1 g of the title compound as a colorless oil. 1.6 of starting material was recovered. 1H NMR (400 MHz, DMSO-d6) δ 10.12 (s, 1H), 8.12 (d, J=6.7 Hz, 1H), 7.63 (d, J=11.0 Hz, 1H) 4.21-4.16 (m, 4H), 1.24 (t, J=7.2 Hz, 6H).

Step 7: methyl 5-bromo-6-(diethoxyphosphoryl)difluoromethyl) benzo[b]thiophene-2-carboxylate A suspended solution of diethyl ((2-bromo-5-fluoro-4-formylphenyl)difluoromethyl)phosphonate 7 (270 mg, 0.69 mmol) and potassium carbonate (201 mg, 1.46 mmol) in 3 mL of anhydrous DMF was degassed with nitrogen for 15 min, then a solution of methyl thioglycolate (70 µL, 0.76 mmol) in 1 mL of anhydrous DMF was added over a period of 30 min. The reaction mixture was stirred at rt overnight. The reaction mixture was heated to 45° C. for 4 h, and cooled to 0° C. Water and ethyl acetate were added, the layers were separated and the aqueous layer was extracted with ethyl acetate. The combined organic layers were washed with brine, dried over MgSO4 and evaporated to dryness. The crude material was purified by column chromatography eluting with 20-50% ethyl acetate/hexanes to afford 190 mg of the title compound as a colorless solid. 1H NMR (400 MHz, DMSO-d6) δ 8.47 (s, 1H), 8.46 (s, 1H), 8.20 (s, 1H) 4.20-4.11 (m, 4H), 3.30 (s, 3H), 1.22 (t, J=7.0 Hz, 6H).

Step 8 Ammonium ((5-bromo-2-(methoxycarbonyl) benzo[b]thiophen-6-yl)difluoromethyl)phosphonate To a stirred solution of methyl 5-bromo-6-((diethoxyphosphoryl)difluoromethyl)benzo[b]thiophene-2-carboxylate (119 mg, 0.26 mmol) in 2.6 mL of anhydrous dichloromethane at rt was added trimethylsilyl bromide (515 µL, 3.9 mmol). The reaction mixture was stirred at rt overnight, concentrated to dryness, co-evaporated with dichloromethane (3×), and methanol (3×). The residue was dissolved in methanol (3 mL), and 5.2 mL of ammonia (0.5M in dioxane) was added. It was stirred for 1 h, concentrated to dryness under vacuum, and the residue was triturated in Et2O (3 mL) to afford 100 mg of the title compound as a colorless powder. 1H NMR (400 MHz, D2O) δ 8.22 (s, 1H), 8.13 (s, 1H), 7.92 (s, 1H), 3.81 (s, 3H), LCMS (M+1): 400.8 and 402.8.

EXAMPLE 9

((5-Bromo-2-(Carboxy)Benzo[B]Thiophen-6-Yl) Difluoromethyl)Phosphonate

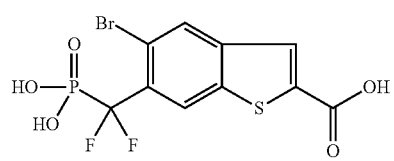 [SMILES: O=C(O)c1cc2cc(Br)c(C(F)(F)P(=O)(O)O)cc2s1]

To a stirred solution of ethyl 5-bromo-6-((diethoxyphosphoryl)difluoromethyl) benzo[b]thiophene-2-carboxylate (100 mg, 0.21 mmol) in 2 mL of anhydrous dichloromethane at rt was added trimethylsilyl bromide (280 µL, 2.12 mmol). The reaction mixture was stirred at rt overnight. LCMS showed the reaction was not complete. It was sonicated for 4 h (bath temperature at 40° C.) and the reaction mixture was concentrated to dryness, co-evaporated with dichloromethane (3×), and ethanol (3×). The residue was dissolved in ethanol (0.5 mL), and water (1.0 mL). 1.0N of NaOH (280 µL, 0.27 mmol) was added to the reaction mixture, and stirred at rt overnight. 20 mL of water and 20 mL of Et2O were added, partitioned, and the aqueous layer was washed with Et 2O then it was treated with 1N HCl to adjust pH at 3, extracted with ethyl acetate (2×). The combined organic layers were washed with brine, dried over MgSO4 and evaporated to dryness. The residue was dissolved in EtOH (2 mL), and 5.4 mL of ammonia (0.5 M in dioxane) was added. It was stirred for 1h, concentrated to dryness under vacuum, and the residue was triturated in Et2O (2 mL) to afford 46 mg of the title compound as a colorless powder. 1H NMR (400 MHz, D2O) δ 8.11 (s, 1H), 8.10 (s, 1H), 7.62 (s, 1H), LCMS (M+1): 386.9 and 388.8.

EXAMPLE 10

(3-Bromo-7-Cyano-2-Naphthyl)(Difluoro)Methylphosphonate

This compound pass prepared as described in WO 2008/089581.

EXAMPLE 11

Enzyme Assay Data on TC-PTP

When tested against TC-PTP, the following inhibitions of enzymatic activity were observed:

| Compound | IC$_{50}$ (µM) |
|---|---|
| Ex. 1 | 0.45 |
| Ex. 2 | 0.26 |
| Ex. 3 | 0.28 |
| Ex. 4 | 1.2 |

-continued

| Compound | IC$_{50}$ (μM) |
|---|---|
| Ex. 5 | 1.5 |
| Ex. 6 | 0.37 |
| Ex. 7 | 0.74 |
| Ex. 8 | 2.9 |
| Ex. 9 | 0.17 |
| Ex. 10 | 0.49 |

EXAMPLE 12

Cell Assay Data for TC-PTP Inhibitor Stimulation of Dendritic Cells

| Compound | % increase in IL-12 production* |
|---|---|
| Ex. 1 | 161 |
| Ex. 2 | 143 |
| Ex. 3 | 130 |
| Ex. 4 | 85 |
| Ex. 5 | 144 |
| Ex. 6 | 60 |
| Ex. 7 | 171 |
| Ex. 10 | 42 |

*24 h IL-12 production following 6 days of DC incubation and maturation in the presence of 32 μM of test compound vs vehicle-treated cells

EXAMPLE 13

Efficacy in Mouse Model of Cancer Using Dcs Activated with the Compound of Example 5

Now referring to FIG. 1 which shows the tumor volume in mice 28 days follow a single treatment of mature dendritic cells activated by either the compound of Example 6 or Example 5. These data show that dendrite cells activated by the compound of Example 5 (which is potent in the 1L-12 release assay shown in Example 12) provides greater efficacy at reducing tumor volume in this model than dendritic cells activated by the compound of Example 6 (which is less potent in the 1L-12 release assay).

EXAMPLE 14

Induction of IL-12 in Human DCS Following Differentiation and Maturation in the Presence and Absence of the Compound of Example 7

Figure 2:
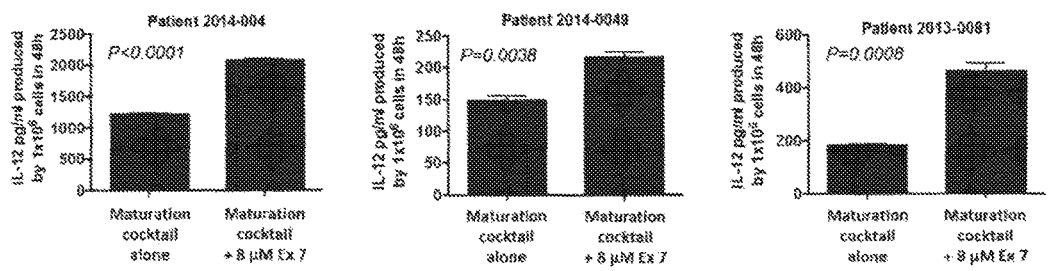
FIG. 2 illustrates the induction of IL-12 in human DCs following differentiation and maturation in the presence and absence of the compound of Example 7.

Now referring to FIG. 2, which shows that dendritic cells derived from monocytes taken from human pancreatic cancer patients, which are matured in the presence of the compound of Example 7, show greater release of IL-12 than the same cells matured without the compound of Example 7. IL-12 release is indicative of the activation state of these cells, and the increase in IL-12 due to the presence of a TC-PTP inhibitor illustrates the utility of the invention.

While preferred embodiments have been described above and illustrated in the accompanying drawings, it will be evident to those skilled, in the art that modifications may be made without departing from this disclosure. Such modifications are considered as possible variants comprised in the scope of the disclosure.

REFERENCES

1. Doody K M, Bourdeau A, Tremblay M L. T-cell protein tyrosine phosphatase is a key regulator in immune cell signaling: lessons from the knockout mouse model and implications in human disease. Immunol Rev. 2009 228: p 325-41
2. Simoncic P D, Lee-Loy A, Barber D L, Tremblay M L, McGlade C J. The T cell protein tyrosine phosphatase is a negative regulator of janus family kinases 1 and 3. Curr Biol. 2002; 12(6):446-453.
3. Tiganis, T., B. E. Kemp, and N. K. Tonks, The protein-tyrosine phosphatase TCPTP regulates epidermal growth factor receptor-mediated and phosphatidylinositol 3-kinase-dependent signaling. J Biol Chem, 1999, 274(39): p. 27768-75.
4. Arimura, Y. and J. Yagi, Comprehensive expression profiles of genes for protein tyrosine phosphatases in immune cells. Sci Signal, 2010, 3(137): p. rs1.
5. Aoki N, Matsuda T. A nuclear protein tyrosine phosphatase TC-PTP is a potential negative regulator of the PRL-mediated signaling pathway: dephosphorylation and deactivation of signal transducer and activator of transcription 5a and 5b by TC-PTP in nucleus. Mol Endocrinol. 2002; 16(1); 58-69.
6. Jackson, S. H. et al. (2006). Dendritic cells loaded with killed allogeneic melanoma cells can induce objective clinical responses and MART-1 specific CD8+ T-cell immunity. J. Immunotherapy, 29, 545-557.
7. Babatz, J. et al. (2003) Large scale immunomagnetic selection of CD14+ monocytes to generate dendritic cells for cancer immunotherapy: a phase 1 study, J. Hematother. Stem Cell Res. 12, 515-523.
8. Stift, A. et al, (2003) Dendritic cell based vaccination in solid cancer, J. Clin. Oncol. 21, 135-142.
9. Brinke, A, et al. (2010) Monophosphoryl lipid A plus IFNγ maturation of dendritic cells induces antigen-specific CD8+ cytotoxic T cells with high cytolytic potential. Cancer Immunol Immunother. 59(8), 1185-95.
10. Banchereau, J.; Palucka, A. K. (2005). Dendritic cells as therapeutic vaccines against cancer. Nat Rev Immunol, 5(4), 296-306.
11. Moll, H. (2004), Antigen delivery by dendrite cells, International. J. of Med. Micro, 294(5), 337-344.

The invention claimed is:
1. An ex vivo method of stimulating an isolated antigen-presenting cell comprising:
    treating isolated antigen presenting cells with an effective amount of a compound of structural Formula Ib, or a pharmaceutically acceptable salts thereof, and stereoisomers thereof:

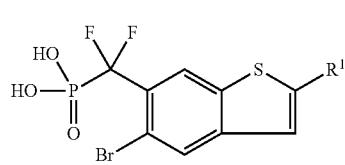

wherein:
    R$^1$ is selected from the group consisting of (a) C$_{1-3}$ alkyl optionally substituted with 1-5 halogens and optionally with one group selected from —OH, —OC$_{1-3}$ alkyl optionally substituted with 1-3 halogens, and —CN; (b) —(C═O)R$^4$; (c) —CN; (d) —(C═O)OR$^4$; (e) —(C═O)NHR$^4$; and (f) —(C═O)NR$^5$R$^6$;
    R$^4$ is selected from the group consisting of (a) H; and (b) C$_{1-3}$ alkyl optionally substituted with 1-5 halogens;

$R^5$ and $R^6$ are independently selected from the group consisting of $C_{1-3}$ alkyl optionally substituted with 1-5 halogens and optionally with one group selected from —OH, and —$OC_{1-3}$ alkyl optionally substituted with 1-3 halogens, wherein said isolated antigen-presenting cell is incubated with an antigen specific to a disease before, during or after said treating said compound, for a time sufficient to obtain an isolated activated antigen-presenting cell wherein the diseases is a cancer.

2. A method for improving or treating a cancer in a patient in need thereof comprising:
   administering an isolated activated antigen presenting cell obtained by the method of claim 1 to said patient,
wherein said cancer causes expression of said antigen specific to the cancer in said patient.

3. The method of claim 1, wherein said isolated antigen presenting cell or said isolated activated antigen presenting cell is a dendritic cell.

4. The method of claim 1, wherein said isolated antigen presenting cell or said isolated activated antigen presenting cell are from the same patient.

5. The method of claim 1, wherein the method further comprises contacting said isolated antigen presenting cells with a maturation cocktail, and wherein said maturation cocktail comprises LPS, MPLA, INFy, CD40L, IL-13, IL-6, TNF-a, PGE-2, or combinations thereof.

6. The method of claim 5, wherein said maturation cocktail is at least one of the following cocktails:
   a) LPS and INFγ;
   b) MPLA and INFγ;
   c) CD40L and INFγ;
   d) IL-1β, IL-6 and TNF-α; and
   e) IL-1β, IL-6, TNF-α and PGE-2.

7. The method of claim 2, wherein said cancer is prostate cancer, breast cancer, ovarian cancer, multiple myeloma, brain cancer, glioma, lung cancer, salivary cancer, stomach cancer, thymic epitherlial cancer, thyroid cancer, leukemia, melanoma, lymphoma, gastric cancer, pancreatic cancer, kidney cancer, bladder cancer, colon cancer and liver cancer.

8. The method of claim 2, wherein said isolated activated antigen presenting cell is administered into the bloodstream of said patient, into a lymph node of said patient, into a tumor of said patient, into a tissue of said patient, or combinations thereof.

9. The method of claim 1, wherein said compound of Formula Ib, or a pharmaceutically acceptable salt thereof, is selected from the following compounds:

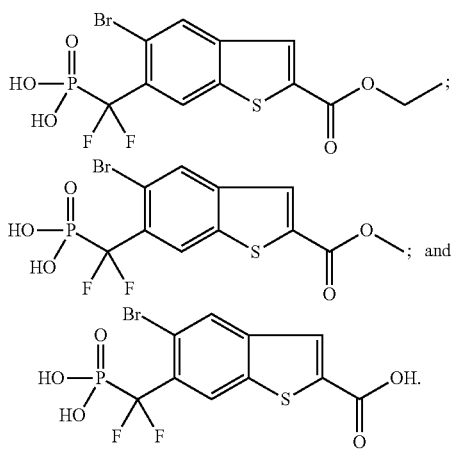

* * * * *